United States Patent [19]
Craig et al.

[11] Patent Number: 5,856,157
[45] Date of Patent: Jan. 5, 1999

[54] $\Delta^9$ 14:0-ACP FATTY ACID DESATURASE AND GENE THEREFOR

[75] Inventors: Richard Craig, State College, Pa.; June I. Medford, Fort Collins, Colo.; Ralph O. Mumma, State College; Diana L. Cox-Foster, Port Matilda, both of Pa.; David Schultz, Haslett, Mich.

[73] Assignee: The Penn State Research Foundation, University Park, Pa.

[21] Appl. No.: 869,137

[22] Filed: Jun. 4, 1997

Related U.S. Application Data

[60] Provisional application No. 60/018,957 Jun. 4, 1996.
[51] Int. Cl.$^6$ .............................. C12N 9/02; C07N 21/04
[52] U.S. Cl. ...................... 435/189; 536/23.1; 536/23.2; 536/23.6; 435/172.1; 435/172.3; 435/410; 435/412; 435/416; 435/417; 435/418; 435/419; 435/69.1; 435/320.1; 800/205
[58] Field of Search ................................ 435/189, 172.1, 435/172.3, 252.3, 252.33, 410, 412, 416–419, 69.1, 320.1; 536/23.1, 23.2, 23.6; 800/205

[56] References Cited

PUBLICATIONS

David J. Schultz et al., "Expression of a $\Delta^9$ 14:0–acyl carrier protein fatty acid desaturase gene is necessary for the production of $\omega^5$ anacardic acids found in pest–resistant geranium (Pelargonium xhortorum)," Proc. Natl. Acad. Sci. USA, vol. 93, pp. 8771–8775, Aug. 1996, Plant Biology.

Edgar B. Cahoon et al., "Characterization of a structurally and functionally diverged acyl–acyl carrier protein desaturase from milkweed seed," Plant Molecular Biology, vol. 33, pp. 1105–1110, 1997.

Cahoon, Edgar B., et al., "Expression of a coriander desaturase results in petroselinic acid production in transgenic tobacco," Proc. Natl. Acad. Sci. USA, vol. 89, pp. 11184–11188, Dec. 1992, Plant Biology.

Cahoon, Edgar B. et al., "$\Delta^6$ Hexadecenoic Acid Is Synthesized by the Activity of a Soluble $\Delta^6$ Palmitoyl–Acyl Carrier Protein Desaturase in *Thunbergia alata* Endosperm," The Journal of Biological Chemistry, vol. 269, No. 44, Nov. 4, 1994, pp. 27519–27526.

Cahoon, Edgar B. et al., "Metabolic Evidence for the Involvement of a $\Delta^4$–Palmitoyl–Acyl Carrier Protein Desaturase in Petroselinic Acid Synthesis in Coriander Endosperm and Transgenic Tobacco Cells," Plant Physiol., (1994) vol. 104, pp. 827–837.

Cahoon, Edgar B. et al., "Modification of the Fatty Acid Composition of *Escherichia coli* by Coexpression of a Plant Acyl–Acyl Carrier Protein Desaturase and Ferredoxin," Journal of Bacteriology, Feb. 1996, vol. 178, No. 3, pp. 936–939.

Cahoon, Edgar B. et al., "Redesign of soluble fatty acid desaturases from plants for altered substrate specificity and double bond position," Proc. Natl. Acad. Sci. USA, vol. 94, pp. 4872–4877, May 1997, Biochemistry.

*Primary Examiner*—Rebecca E. Prouty
*Assistant Examiner*—Nashaat T. Nashed
*Attorney, Agent, or Firm*—Thomas J. Monahan

[57] ABSTRACT

Isolation and characterization of a novel plant fatty acid desaturase cDNA that encodes a $\Delta^9$ 14:0-ACP desaturase. Expression of the $\Delta^9$ 14:0-ACP desaturase is a critical factor for pest resistance in plants of the genus Pelargonium and other plants generally; the desaturase gene is also useful in other contexts and for other purposes such as increasing the percentage of unsaturated fatty acids in oil-producing crops such as soybeans, rapeseed, maize, sunflower, safflower, cotton, cuphea, peanut, coconut and oil-palm, as well as increasing the percentage of unsaturated fatty acids in other plants generally.

7 Claims, 13 Drawing Sheets

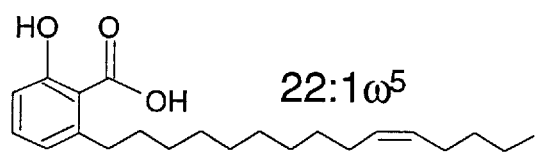
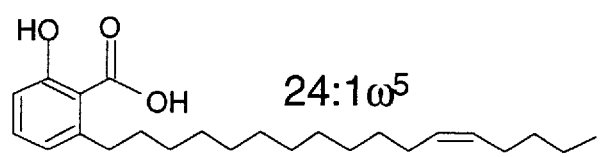
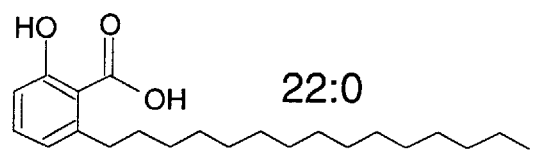
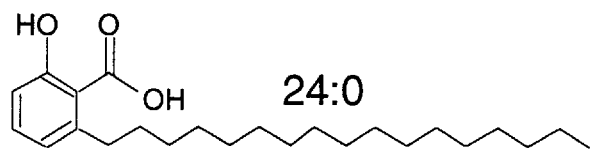
Fig. 2

```
ATAGAAGATGGGTGTTCTACTTAACATATGTTCCTCTCCATTTCCAGTAGTAGCATCTGCTGCT(64)
         *m  g  v  l  l  n  i  c  s  s  p  f  p  v  v  a  s  a  A

TCTACTTCCATTTCCAAGGTTAATCATATAAGAAAAGTTGGAGTAACTGGTGTAATGGCTCCCCAA(130)
 S  T  S  I  S  K  V  N  H  I  R  K  V  G  V  T  G  V  M  A  P  Q

AAAATAGAAATATTCAAATCTATGGAGGAATGGGGTAAGCACAACATTTTGCCACTGGCGAAACCA(196)
 K  I  E  I  F  K  S  M  E  E  W  G  K  H  N  I  L  P  L  A  K  P

GTTGAAAAATCATGGCAACCAACAGACTTTTTGCCGGACCCTTCCTCCGAAGGATTCATGGAAGAA(262)
 V  E  K  S  W  Q  P  T  D  F  L  P  D  P  S  S  E  G  F  M  E  E

TATAATGCATTTAAGGAGAGGACGAGAGAGCTTCCAGACGAATACTTCGTTGTTTTGGCGGGCGAT(328)
 Y  N  A  F  K  E  R  T  R  E  L  P  D  E  Y  F  V  V  L  A  G  D

ATGATTACGGAAGAGGCTCTTCCTACCTACCAAACATTGGTGAACAGGCCAGATGAAGTTGCAGAT(394)
 M  I  T  E  E  A  L  P  T  Y  Q  T  L  V  N  R  P  D  E  V  A  D

GAAACAGGCCACAGTGAGAGCCCGTGGGCAGTTTGGTCGAGGGCGTGGACTGCAGAAGAAAATAGG(460)
 E  T  G  H  S  E  S  P  W  A  V  W  S  R  A  W  T  A  E  E  N  R

CACGGCGATCTTCTCAACAAGTACTTGTACCTCTCGGGGAAGCTTGACATGAGACAAGTAGAGAAG(526)
 H  G  D  L  L  N  K  Y  L  Y  L  S  G  K  L  D  M  R  Q  V  E  K

ACCATTCAATATCTCATTGCCTTAGGACAGGACATCGGAACCGAAAAGAACCCCTACCACTTGTTT(592)
 T  I  Q  Y  L  I  A  L  G  Q  D  I  G  T  E  K  N  P  Y  H  L  F

ATATACACGTCATTTCAAGAAAGGGCAACATTCATTTCCCACGCAAATACCGCAAAACTAGCCCAG(658)
 I  Y  T  S  F  Q  E  R  A  T  F  I  S  H  A  N  T  A  K  L  A  Q

CAACACGGGGACAAGCAACTTGCCCAAATATGCGGTACCATCGCCGCGGACGAGAAGCGCCACGAA(724)
 Q  H  G  D  K  Q  L  A  Q  I  C  G  T  I  A  A  D  E  K  R  H  E

ACGGCATACACCCGCATAGTTGACAAGCTTTTTGAGTTGGATCCAGACGAAACAATGTCCTGCCTC(790)
 T  A  Y  T  R  I  V  D  K  L  F  E  L  D  P  D  E  T  M  S  C  L

GCCCACATGATGAAGAGGAAGATCACAATGCCGGCTCACCTAATGCGCGATGGTCGAGACCCGCAT(856)
 A  H  M  M  K  R  K  I  T  M  P  A  H  L  M  R  D  G  R  D  P  H

TTGTTCCAACACTTCTCGGTGGTAGCGTCTCGAACAGGGGTGTATACGGTGATGGACTATATAAAT(922)
 L  F  Q  H  F  S  V  V  A  S  R  T  G  V  Y  T  V  M  D  Y  I  N

ATACTGGAGCATTTTGTGGAGAAGTGGAATATCGAGAAGATAACGGCAGGGCTTTCAGATAAGGGA(988)
 I  L  E  H  F  V  E  K  W  N  I  E  K  I  T  A  G  L  S  D  K  G

AGGGAAGCTCAGGATTACGTTTGCAAGTTAGGTGAAAGGTTAAGAAAAGTGGAGGAGAGGGCTCAT(1054)
 R  E  A  Q  D  Y  V  C  K  L  G  E  R  L  R  K  V  E  E  R  A  H

CAAAGAGTCGTACAAGCTGACCCTATTCCATTTAGCTGGATATTTGATAGAAAAGTCTAGTGGTAT(1120)
 Q  R  V  V  Q  A  D  P  I  P  F  S  W  I  F  D  R  K  V  *

ATCTATAAAGTTAAAATAAGGGTACTCCGTAATATTTTTCTAAAAAGATTACAACTATAAAAATAA(1186)
GTTTTTAGAAAAAATCTGGGGTCGACTGACCCCAATTGAACCATGTAGTTCCGCTACTGTTTATAT(1252)
ATTTACGTATTTTCATCGTC                                          (1272)
```

Fig. 3

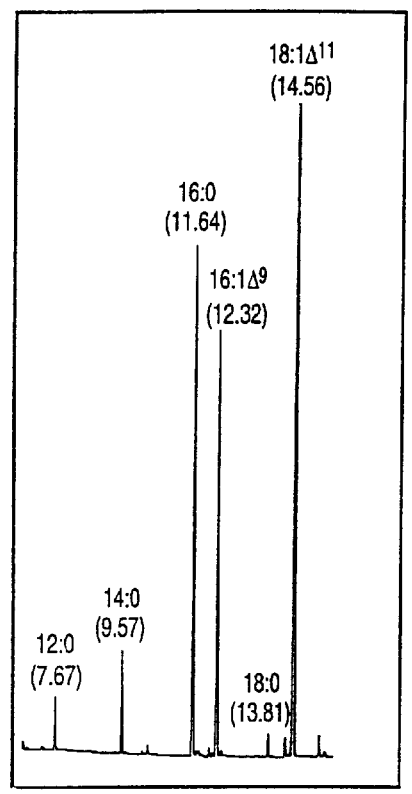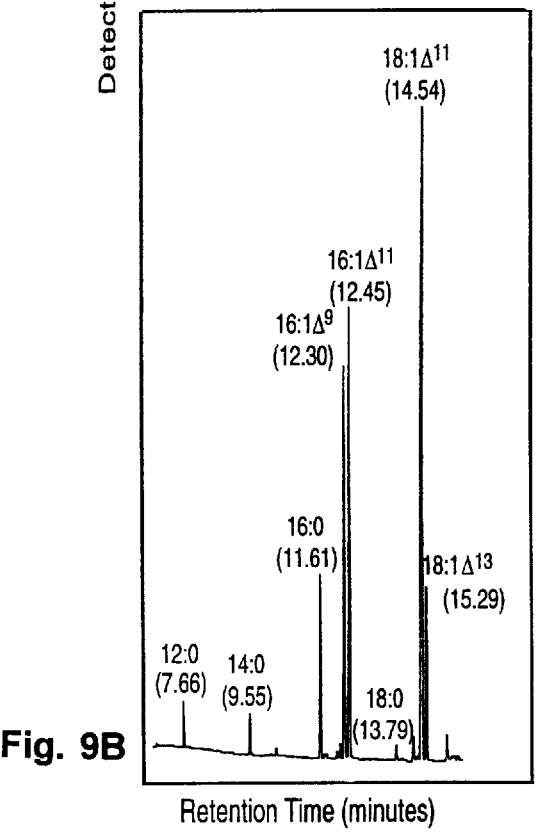

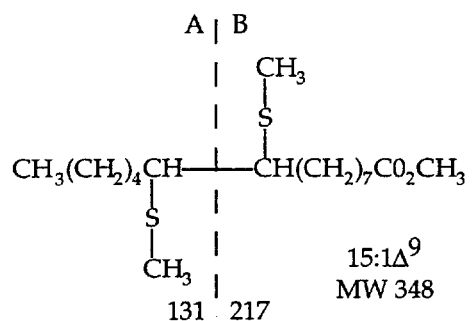
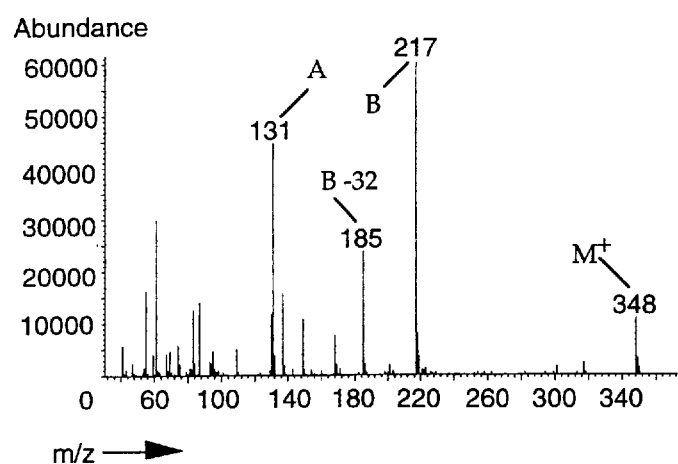
Fig. 12

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 1272 base pairs
    ( B ) TYPE: nucleic acid
    ( C ) STRANDEDNESS: single
    ( D ) TOPOLOGY: linear ( i x ) FEATURE:
    ( A ) NAME/KEY: Coding Sequence
    ( B ) LOCATION: 8...1111
    ( D ) OTHER INFORMATION:

( x i ) SEQUENCE DESCRIPTION: SEQ ID NO:1:

```
ATAGAAG ATG GGT GTT CTA CTT AAC ATA TGT TCC TCT CCA TTT CCA GTA         49
        Met Gly Val Leu Leu Asn Ile Cys Ser Ser Pro Phe Pro Val
        1           5                       10

GTA GCA TCT GCT GCT TCT ACT TCC ATT TCC AAG GTT AAT CAT ATA AGA         97
```

|     |     |     |     |     |     |     |     |     |     |     |     |     |     |     |     |
|-----|-----|-----|-----|-----|-----|-----|-----|-----|-----|-----|-----|-----|-----|-----|-----|
| Val | Ala | Ser | Ala | Ala | Ser | Thr | Ser | Ile | Ser | Lys | Val | Asn | His | Ile | Arg |
| 15  |     |     |     | 20  |     |     |     |     | 25  |     |     |     |     | 30  |     |

| AAA | GTT | GGA | GTA | ACT | GGT | GTA | ATG | GCT | CCC | CAA | AAA | ATA | GAA | ATA | TTC | 145 |
|-----|-----|-----|-----|-----|-----|-----|-----|-----|-----|-----|-----|-----|-----|-----|-----|-----|
| Lys | Val | Gly | Val | Thr | Gly | Val | Met | Ala | Pro | Gln | Lys | Ile | Glu | Ile | Phe |     |
|     |     |     |     | 35  |     |     |     |     | 40  |     |     |     |     | 45  |     |     |

| AAA | TCT | ATG | GAG | GAA | TGG | GGT | AAG | CAC | AAC | ATT | TTG | CCA | CTG | GCG | AAA | 193 |
|-----|-----|-----|-----|-----|-----|-----|-----|-----|-----|-----|-----|-----|-----|-----|-----|-----|
| Lys | Ser | Met | Glu | Glu | Trp | Gly | Lys | His | Asn | Ile | Leu | Pro | Leu | Ala | Lys |     |
|     |     |     | 50  |     |     |     |     | 55  |     |     |     |     | 60  |     |     |     |

| CCA | GTT | GAA | AAA | TCA | TGG | CAA | CCA | ACA | GAC | TTT | TTG | CCG | GAC | CCT | TCC | 241 |
|-----|-----|-----|-----|-----|-----|-----|-----|-----|-----|-----|-----|-----|-----|-----|-----|-----|
| Pro | Val | Glu | Lys | Ser | Trp | Gln | Pro | Thr | Asp | Phe | Leu | Pro | Asp | Pro | Ser |     |
|     |     | 65  |     |     |     |     | 70  |     |     |     |     | 75  |     |     |     |     |

| TCC | GAA | GGA | TTC | ATG | GAA | GAA | TAT | AAT | GCA | TTT | AAG | GAG | AGG | ACG | AGA | 289 |
|-----|-----|-----|-----|-----|-----|-----|-----|-----|-----|-----|-----|-----|-----|-----|-----|-----|
| Ser | Glu | Gly | Phe | Met | Glu | Glu | Tyr | Asn | Ala | Phe | Lys | Glu | Arg | Thr | Arg |     |
|     |     | 80  |     |     |     |     | 85  |     |     |     |     | 90  |     |     |     |     |

| GAG | CTT | CCA | GAC | GAA | TAC | TTC | GTT | GTT | TTG | GCG | GGC | GAT | ATG | ATT | ACG | 337 |
|-----|-----|-----|-----|-----|-----|-----|-----|-----|-----|-----|-----|-----|-----|-----|-----|-----|
| Glu | Leu | Pro | Asp | Glu | Tyr | Phe | Val | Val | Leu | Ala | Gly | Asp | Met | Ile | Thr |     |
| 95  |     |     |     |     | 100 |     |     |     |     | 105 |     |     |     |     | 110 |     |

| GAA | GAG | GCT | CTT | CCT | ACC | TAC | CAA | ACA | TTG | GTG | AAC | AGG | CCA | GAT | GAA | 385 |
|-----|-----|-----|-----|-----|-----|-----|-----|-----|-----|-----|-----|-----|-----|-----|-----|-----|
| Glu | Glu | Ala | Leu | Pro | Thr | Tyr | Gln | Thr | Leu | Val | Asn | Arg | Pro | Asp | Glu |     |
|     |     |     |     | 115 |     |     |     |     | 120 |     |     |     |     | 125 |     |     |

| GTT | GCA | GAT | GAA | ACA | GGC | CAC | AGT | GAG | AGC | CCG | TGG | GCA | GTT | TGG | TCG | 433 |
|-----|-----|-----|-----|-----|-----|-----|-----|-----|-----|-----|-----|-----|-----|-----|-----|-----|
| Val | Ala | Asp | Glu | Thr | Gly | His | Ser | Glu | Ser | Pro | Trp | Ala | Val | Trp | Ser |     |
|     |     |     | 130 |     |     |     |     | 135 |     |     |     |     | 140 |     |     |     |

| AGG | GCG | TGG | ACT | GCA | GAA | GAA | AAT | AGG | CAC | GGC | GAT | CTT | CTC | AAC | AAG | 481 |
|-----|-----|-----|-----|-----|-----|-----|-----|-----|-----|-----|-----|-----|-----|-----|-----|-----|
| Arg | Ala | Trp | Thr | Ala | Glu | Glu | Asn | Arg | His | Gly | Asp | Leu | Leu | Asn | Lys |     |
|     |     |     | 145 |     |     |     |     | 150 |     |     |     |     | 155 |     |     |     |

| TAC | TTG | TAC | CTC | TCG | GGG | AAG | CTT | GAC | ATG | AGA | CAA | GTA | GAG | AAG | ACC | 529 |
|-----|-----|-----|-----|-----|-----|-----|-----|-----|-----|-----|-----|-----|-----|-----|-----|-----|
| Tyr | Leu | Tyr | Leu | Ser | Gly | Lys | Leu | Asp | Met | Arg | Gln | Val | Glu | Lys | Thr |     |
|     | 160 |     |     |     |     | 165 |     |     |     |     | 170 |     |     |     |     |     |

| ATT | CAA | TAT | CTC | ATT | GCC | TTA | GGA | CAG | GAC | ATC | GGA | ACC | GAA | AAG | AAC | 577 |
|-----|-----|-----|-----|-----|-----|-----|-----|-----|-----|-----|-----|-----|-----|-----|-----|-----|
| Ile | Gln | Tyr | Leu | Ile | Ala | Leu | Gly | Gln | Asp | Ile | Gly | Thr | Glu | Lys | Asn |     |
| 175 |     |     |     |     | 180 |     |     |     |     | 185 |     |     |     |     | 190 |     |

| CCC | TAC | CAC | TTG | TTT | ATA | TAC | ACG | TCA | TTT | CAA | GAA | AGG | GCA | ACA | TTC | 625 |
|-----|-----|-----|-----|-----|-----|-----|-----|-----|-----|-----|-----|-----|-----|-----|-----|-----|
| Pro | Tyr | His | Leu | Phe | Ile | Tyr | Thr | Ser | Phe | Gln | Glu | Arg | Ala | Thr | Phe |     |
|     |     |     |     | 195 |     |     |     |     | 200 |     |     |     |     | 205 |     |     |

| ATT | TCC | CAC | GCA | AAT | ACC | GCA | AAA | CTA | GCC | CAG | CAA | CAC | GGG | GAC | AAG | 673 |
|-----|-----|-----|-----|-----|-----|-----|-----|-----|-----|-----|-----|-----|-----|-----|-----|-----|
| Ile | Ser | His | Ala | Asn | Thr | Ala | Lys | Leu | Ala | Gln | Gln | His | Gly | Asp | Lys |     |
|     |     |     | 210 |     |     |     |     | 215 |     |     |     |     | 220 |     |     |     |

| CAA | CTT | GCC | CAA | ATA | TGC | GGT | ACC | ATC | GCC | GCG | GAC | GAG | AAG | CGC | CAC | 721 |
|-----|-----|-----|-----|-----|-----|-----|-----|-----|-----|-----|-----|-----|-----|-----|-----|-----|
| Gln | Leu | Ala | Gln | Ile | Cys | Gly | Thr | Ile | Ala | Ala | Asp | Glu | Lys | Arg | His |     |
|     |     |     | 225 |     |     |     |     | 230 |     |     |     |     | 235 |     |     |     |

| GAA | ACG | GCA | TAC | ACC | CGC | ATA | GTT | GAC | AAG | CTT | TTT | GAG | TTG | GAT | CCA | 769 |
|-----|-----|-----|-----|-----|-----|-----|-----|-----|-----|-----|-----|-----|-----|-----|-----|-----|
| Glu | Thr | Ala | Tyr | Thr | Arg | Ile | Val | Asp | Lys | Leu | Phe | Glu | Leu | Asp | Pro |     |
|     | 240 |     |     |     |     | 245 |     |     |     |     | 250 |     |     |     |     |     |

| GAC | GAA | ACA | ATG | TCC | TGC | CTC | GCC | CAC | ATG | ATG | AAG | AGG | AAG | ATC | ACA | 817 |
|-----|-----|-----|-----|-----|-----|-----|-----|-----|-----|-----|-----|-----|-----|-----|-----|-----|
| Asp | Glu | Thr | Met | Ser | Cys | Leu | Ala | His | Met | Met | Lys | Arg | Lys | Ile | Thr |     |
| 255 |     |     |     |     | 260 |     |     |     |     | 265 |     |     |     |     | 270 |     |

| ATG | CCG | GCT | CAC | CTA | ATG | CGC | GAT | GGT | CGA | GAC | CCG | CAT | TTG | TTC | CAA | 865 |
|-----|-----|-----|-----|-----|-----|-----|-----|-----|-----|-----|-----|-----|-----|-----|-----|-----|
| Met | Pro | Ala | His | Leu | Met | Arg | Asp | Gly | Arg | Asp | Pro | His | Leu | Phe | Gln |     |
|     |     |     |     | 275 |     |     |     |     | 280 |     |     |     |     | 285 |     |     |

| CAC | TTC | TCG | GTG | GTA | GCG | TCT | CGA | ACA | GGG | GTG | TAT | ACG | GTG | ATG | GAC | 913 |
|-----|-----|-----|-----|-----|-----|-----|-----|-----|-----|-----|-----|-----|-----|-----|-----|-----|
| His | Phe | Ser | Val | Val | Ala | Ser | Arg | Thr | Gly | Val | Tyr | Thr | Val | Met | Asp |     |
|     |     |     | 290 |     |     |     |     | 295 |     |     |     |     | 300 |     |     |     |

| TAT | ATA | AAT | ATA | CTG | GAG | CAT | TTT | GTG | GAG | AAG | TGG | AAT | ATC | GAG | AAG | 961 |
|-----|-----|-----|-----|-----|-----|-----|-----|-----|-----|-----|-----|-----|-----|-----|-----|-----|
| Tyr | Ile | Asn | Ile | Leu | Glu | His | Phe | Val | Glu | Lys | Trp | Asn | Ile | Glu | Lys |     |
|     |     | 305 |     |     |     |     | 310 |     |     |     |     | 315 |     |     |     |     |

| ATA | ACG | GCA | GGG | CTT | TCA | GAT | AAG | GGA | AGG | GAA | GCT | CAG | GAT | TAC | GTT | 1009 |
|-----|-----|-----|-----|-----|-----|-----|-----|-----|-----|-----|-----|-----|-----|-----|-----|------|
| Ile | Thr | Ala | Gly | Leu | Ser | Asp | Lys | Gly | Arg | Glu | Ala | Gln | Asp | Tyr | Val |      |
|     | 320 |     |     |     |     | 325 |     |     |     |     | 330 |     |     |     |     |      |

| TGC | AAG | TTA | GGT | GAA | AGG | TTA | AGA | AAA | GTG | GAG | GAG | AGG | GCT | CAT | CAA | 1057 |
|-----|-----|-----|-----|-----|-----|-----|-----|-----|-----|-----|-----|-----|-----|-----|-----|------|

```
Cys  Lys  Leu  Gly  Glu  Arg  Leu  Arg  Lys  Val  Glu  Glu  Arg  Ala  His  Gln
335                 340                 345                 350

AGA  GTC  GTA  CAA  GCT  GAC  CCT  ATT  CCA  TTT  AGC  TGG  ATA  TTT  GAT  AGA         1105
Arg  Val  Val  Gln  Ala  Asp  Pro  Ile  Pro  Phe  Ser  Trp  Ile  Phe  Asp  Arg
                    355                 360                      365

AAA  GTC   TAGTGGTATA  TCTATAAAGT  TAAAATAAGG  GTACTCCGTA  ATATTTTCT  AA              1163
Lys  Val

AAAGATTACA  ACTATAAAAA  TAAGTTTTTA  GAAAAAATCT  GGGGTCGACT  GACCCCAATT                 1223

GAACCATGTA  GTTCCGCTAC  TGTTTATATA  TTTACGTATT  TTCATCGTC                              1272
```

(2) INFORMATION FOR SEQ ID NO:2:

(i) SEQUENCE CHARACTERISTICS:
        (A) LENGTH: 368 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met  Gly  Val  Leu  Leu  Asn  Ile  Cys  Ser  Ser  Pro  Phe  Pro  Val  Val  Ala
 1                   5                  10                       15

Ser  Ala  Ala  Ser  Thr  Ser  Ile  Ser  Lys  Val  Asn  His  Ile  Arg  Lys  Val
                20                  25                       30

Gly  Val  Thr  Gly  Val  Met  Ala  Pro  Gln  Lys  Ile  Glu  Ile  Phe  Lys  Ser
           35                  40                       45

Met  Glu  Glu  Trp  Gly  Lys  His  Asn  Ile  Leu  Pro  Leu  Ala  Lys  Pro  Val
      50                  55                       60

Glu  Lys  Ser  Trp  Gln  Pro  Thr  Asp  Phe  Leu  Pro  Asp  Pro  Ser  Ser  Glu
 65                      70                       75                        80

Gly  Phe  Met  Glu  Glu  Tyr  Asn  Ala  Phe  Lys  Glu  Arg  Thr  Arg  Glu  Leu
                     85                       90                        95

Pro  Asp  Glu  Tyr  Phe  Val  Val  Leu  Ala  Gly  Asp  Met  Ile  Thr  Glu  Glu
               100                      105                      110

Ala  Leu  Pro  Thr  Tyr  Gln  Thr  Leu  Val  Asn  Arg  Pro  Asp  Glu  Val  Ala
               115                      120                      125

Asp  Glu  Thr  Gly  His  Ser  Glu  Ser  Pro  Trp  Ala  Val  Trp  Ser  Arg  Ala
     130                      135                      140

Trp  Thr  Ala  Glu  Glu  Asn  Arg  His  Gly  Asp  Leu  Leu  Asn  Lys  Tyr  Leu
145                      150                      155                      160

Tyr  Leu  Ser  Gly  Lys  Leu  Asp  Met  Arg  Gln  Val  Glu  Lys  Thr  Ile  Gln
                165                      170                      175

Tyr  Leu  Ile  Ala  Leu  Gly  Gln  Asp  Ile  Gly  Thr  Glu  Lys  Asn  Pro  Tyr
                180                      185                      190

His  Leu  Phe  Ile  Tyr  Thr  Ser  Phe  Gln  Glu  Arg  Ala  Thr  Phe  Ile  Ser
           195                      200                      205

His  Ala  Asn  Thr  Ala  Lys  Leu  Ala  Gln  Gln  His  Gly  Asp  Lys  Gln  Leu
     210                      215                      220

Ala  Gln  Ile  Cys  Gly  Thr  Ile  Ala  Ala  Asp  Glu  Lys  Arg  His  Glu  Thr
225                      230                      235                      240

Ala  Tyr  Thr  Arg  Ile  Val  Asp  Lys  Leu  Phe  Glu  Leu  Asp  Pro  Asp  Glu
                245                      250                      255

Thr  Met  Ser  Cys  Leu  Ala  His  Met  Met  Lys  Arg  Lys  Ile  Thr  Met  Pro
                260                      265                      270
```

| | | | | | | | | | | | | | | |
|---|---|---|---|---|---|---|---|---|---|---|---|---|---|---|
| Ala | His | Leu 275 | Met | Arg | Asp | Gly | Arg 280 | Asp | Pro | His | Leu | Phe 285 | Gln | His | Phe |
| Ser | Val 290 | Val | Ala | Ser | Arg | Thr 295 | Gly | Val | Tyr | Thr | Val 300 | Met | Asp | Tyr | Ile |
| Asn 305 | Ile | Leu | Glu | His | Phe 310 | Val | Glu | Lys | Trp | Asn 315 | Ile | Glu | Lys | Ile | Thr 320 |
| Ala | Gly | Leu | Ser | Asp 325 | Lys | Gly | Arg | Glu | Ala 330 | Gln | Asp | Tyr | Val | Cys 335 | Lys |
| Leu | Gly | Glu | Arg 340 | Leu | Arg | Lys | Val | Glu 345 | Glu | Arg | Ala | His | Gln 350 | Arg | Val |
| Val | Gln | Ala 355 | Asp | Pro | Ile | Pro | Phe 360 | Ser | Trp | Ile | Phe | Asp 365 | Arg | Lys | Val |

$\Delta^9$ 14:0-ACP FATTY ACID DESATURASE AND GENE THEREFOR

CROSS-REFERENCE TO RELATED APPLICATIONS

This application claims the benefits based upon U.S. Provisional Application Serial No. 60/018,957 filed Jun. 4, 1996.

FIELD OF THE INVENTION

The present invention relates to a novel fatty acid desaturase gene and its unique uses in a variety of applications including imparting pest resistance in plants of the genus Pelargonium and in the enhancement of natural and synthetic fatty acids and their reaction products. The expression of the gene defines a trichome specific promoter; trichome specific promoters can be used for direct expression of this or other genes.

BACKGROUND OF THE INVENTION

In the garden geranium (*Pelargonium xhortorum*), inbred genotypes resistant to pests (e.g., spider mites and aphids) and inbred genotypes susceptible to pests, have been identified (Gerhold et al., 1984; Walters et al., 1990a) (FIG. 3.1). Pest-resistant and pest-susceptible plants produce anacardic acids (6-alkyl-salicylic acid) in exudates of tall glandular trichomes. However, the composition of anacardic acids differs between resistant and susceptible genotypes (Hesk et al., 1991; Grazzini et al., 1995). The trichome exudate from the resistant genotype has a predominance (~81% of exudate profile) of unsaturated 22:1 $\omega^5$ and 24:1 $\omega^5$ anacardic acids. In contrast, trichome exudates from the susceptible genotype lack the $\omega^5$ products and have saturated 22:0 and 24:0 anacardic acids (FIG. 3.2) (Hesk et al., 1991; Grazzini et al., 1995).

The desaturation status of the anacardic acid exudate affects the physical properties of the exudate and the effectiveness of pest resistance. The anacardic acid exudate of the resistant genotype is fluid and acts as a "sticky trap" that impedes the pest movement and adheres to their exoskeletons (Walters et al., 1990a; Walters et al., 1989). This results in enhanced pest exposure to anacardic acids which have toxic properties and have been shown to inhibit enzymatic steps in pest reproduction (Gerhold et al., 1984; Grazzini et al., 1991). In contrast, the anacardic acid exudate of the susceptible genotype is solid, does not act as an effective "sticky trap", and does not adhere to the exoskeleton; therefore, exposure to the toxic exudate is minimized.

Fatty acids have been shown to be direct precursors of anacardic acids. Saturated and unsaturated [$^{14}$C]-labeled fatty acids applied to floral tissue and leaves produce corresponding [$^{14}$C]-labeled saturated and unsaturated anacardic acids (Walters et al., 1990b; Hesk et al., 1992). The production of anacardic acids is consistent with the addition of six carbons to the labeled fatty acid (e.g., supplying a 16:0 fatty acid results in the production of a 22:0 anacardic acid) (Walters et al., 1990b; Hesk et al., 1992). Thus the novel 16:1 $\Delta^{11}$ and 18:1 $\Delta^{13}$ fatty acids are direct precursors to the 22:1 $\omega^5$ and 24:1 $\omega^5$ anacardic acids (respectively), which are associated with pest resistance (Walters et al., 1990b; Hesk et al., 1992). Consistent with this, the 16:1 $\Delta^{11}$ and 18:1 $\Delta^{13}$ fatty acids and corresponding $\omega$5 anacardic acids are specifically localized in the trichomes of the resistant genotype (Hesk et al., 1991; Grazzini et al., 1995; Yerger et al., 1992).

Early analysis of inbred resistant and susceptible genotypes suggested that pest resistance is correlated with a quantitative difference in the levels of $\omega$5 anacardic acids (Gerhold et al., 1984; Walters et al., 1990a; Walters et al., 1989; Craig et al., 1986; Walters et al., 1990c). Subsequent refinement of the anacardic acid analysis showed that $\omega^5$ anacardic acids are either present at high levels in the resistant plants or undetectable in the susceptible plants (Hesk et al., 1991; Grazzini et al., 1995). Analysis of an $F_2$ population (n=160) resulting from a cross of inbred resistant and inbred susceptible genotypes confirmed a 3:1 segregation ratio ($X^2$=0.03, P$\geq$0.86) for a single dominant locus controlling the production of $\omega^5$ anacardic acids (Grazzini, 1993). To confirm the association between $\omega^5$ anacardic acids and pest resistance, 10 plants containing, and 9 plants lacking, $\omega^5$ anacardic acids were subjected to mite bioassays. All plants containing $\omega^5$ anacardic acids were pest-resistant, and all plants deficient for $\omega^5$ anacardic acids were pest-susceptible (Grazzini, 1993). Accordingly, a need remained both to identify the gene responsible for the pest-resistance as well as the applications of that gene in pest-resistance and other technologies.

BRIEF DESCRIPTION OF THE INVENTION

The present invention inheres in the isolation and characterization of a novel plant fatty acid desaturase cDNA that encodes a $\Delta^9$ 14:0-ACP desaturase. We demonstrate a close correlation between expression of this desaturase and the accumulation of 16:1 $\Delta^{11}$ and 18:1 $\Delta^{13}$ fatty acids and 22:1 $\omega^5$ and 24:1 $\omega^5$ anacardic acids, as well as to the pest-resistant genotype of garden geraniums. Collectively, these data indicate that expression of the $\Delta^9$ 14:0-ACP desaturase is a critical factor for pest resistance in geraniums and other plants generally. The expression of the gene defines a trichome specific promoter; trichome specific promoters can be used for direct expression of this or other genes.

The gene itself can also be introduced into other cells either to alter or to enhance the production of, as a single example, oil in those cells. For example, in some instances having a higher percentage of unsaturated fatty acids in an edible oil—or in other oils—is commercially and agriculturally important when it can be attained. Oil-producing crops in which such an innovation is useful include (without limitation) soybeans, rapeseed, maize, sunflower, safflower, cotton, cuphea, peanut, coconut, and oil-palm. Published and patented literature addressing this application includes, for example, U.S. Pat. No. 5,057,419 to Martin et al. Oils not necessarily thought of as edible—such as pelargonium oil itself—or definitely other than edible may also be engineered using the present gene and desaturase(s). The manner in which the gene is introduced into the plant host cell is not critical to the invention, and any manner of transformation may be employed such as electroporation, liposome fusion, DNA bombardments, etc. Again, the expression of the gene defines a trichome specific promoter; trichome specific promoters can be used for direct expression of this or other genes. The gene and its expression products can also be used in connection with manufacturing methods known in the art, for example, in innovative processes for making specialty polymers such as NYLON and other methods in which unsaturated fatty acids are used as constituents or starting materials.

BRIEF DESCRIPTION OF THE DRAWINGS

FIG. 2 shows a contrast view of structures of anacardic acids;

FIG. 3 is the cDNA and deduced amino acid sequence of the type B desaturase clone, SEQ ID NO: 1 and SEQ ID NO: 2, respectively;

FIGS. 9a and 9b shows gas chromatogram of *E. coli* fatty acid methyl esters;

FIG. 12 is a mass spectral analysis of double bond position of in vitro desaturation product of dimethyl disulfide adducts of 15:1 fatty acid methyl esters product.

DETAILED DESCRIPTION OF THE INVENTION

Figure 1:
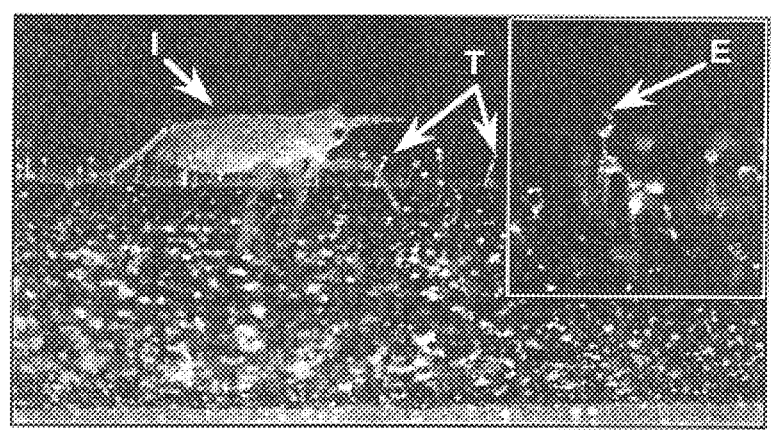
FIG. 1 is a geranium flower pedicel of the pest-resistant genotype covered with the glandular trichomes.
Figure 4:
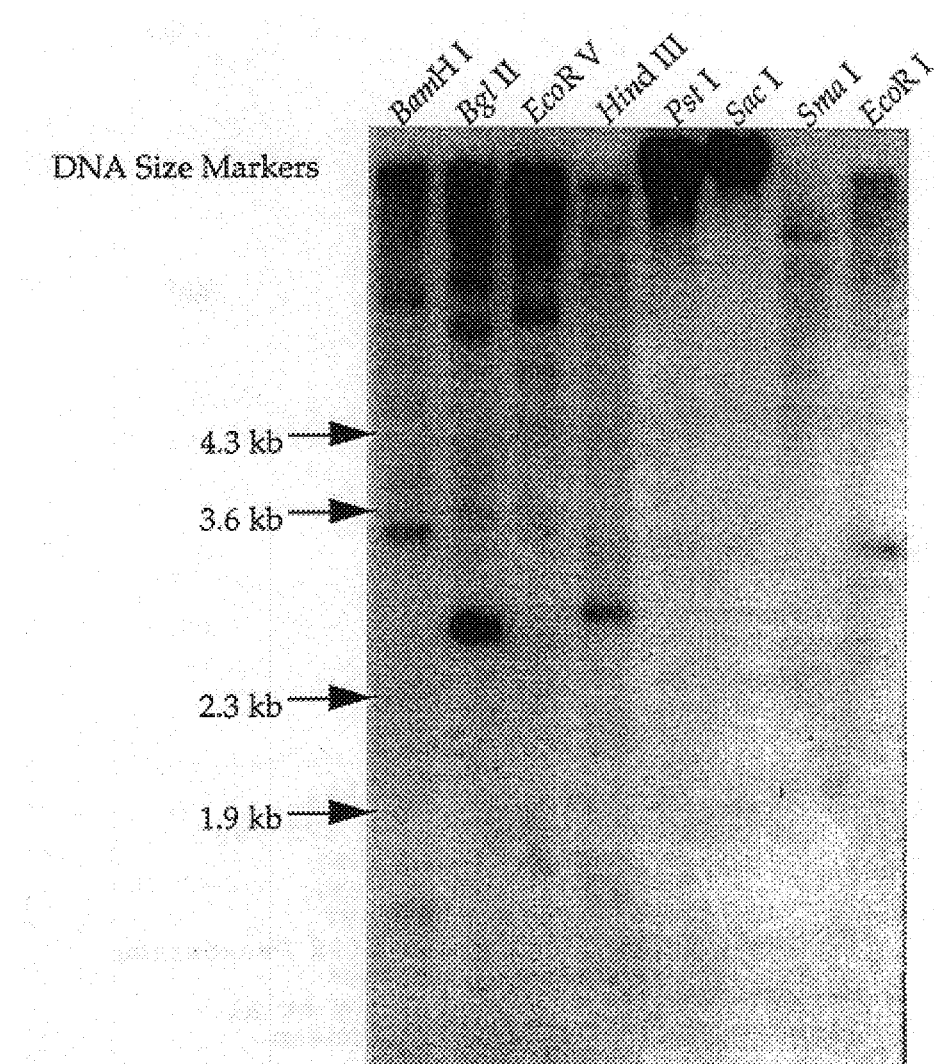
FIG. 4 is a southern blot analysis of acyl-ACP desaturases in geranium.
Figure 5:
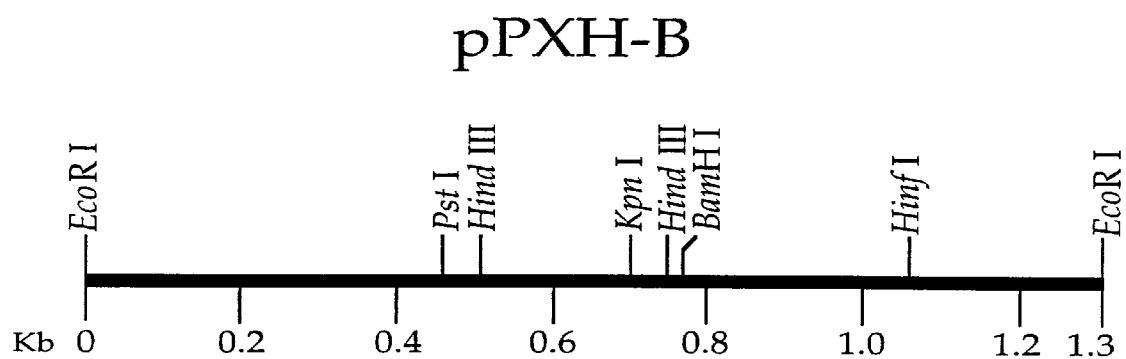
FIG. 5 shows restriction endonuclease map of pPXH-B.
Figure 6:
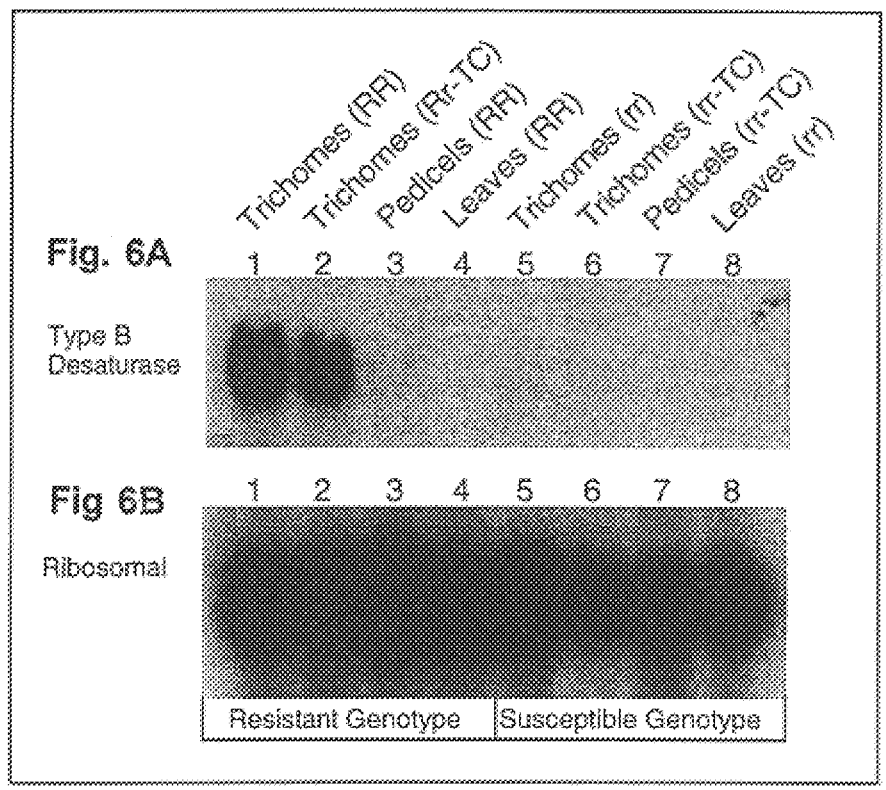
FIGS. 6a and 6B shows expression of the type B desaturase.
Figure 7:
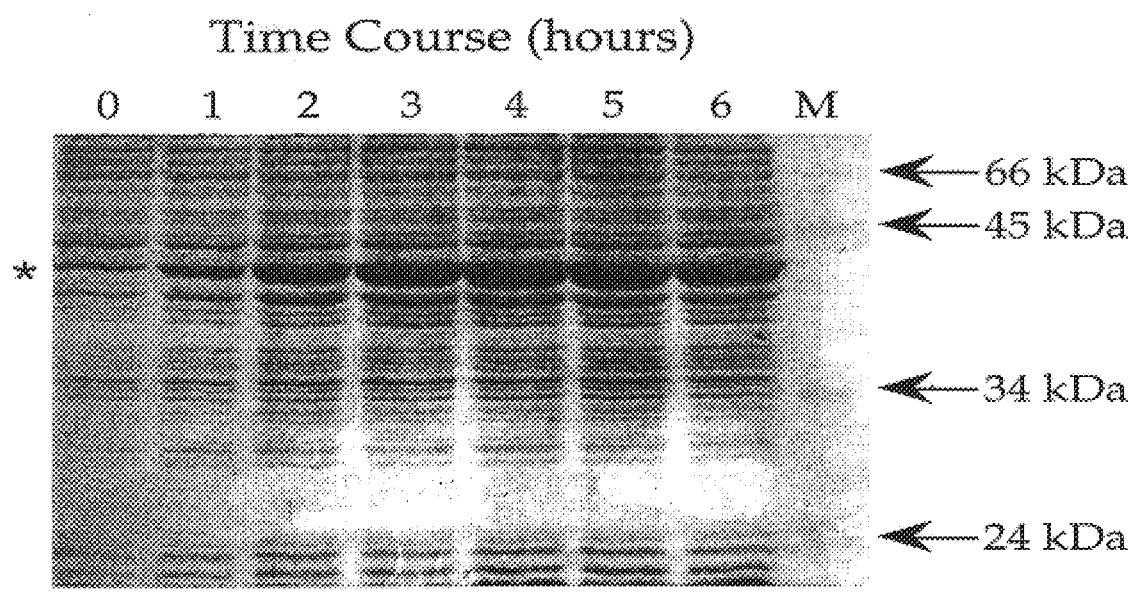
FIG. 7 is time course protein induction of the type B desaturase clone (pPXH-B)
Figure 8A:
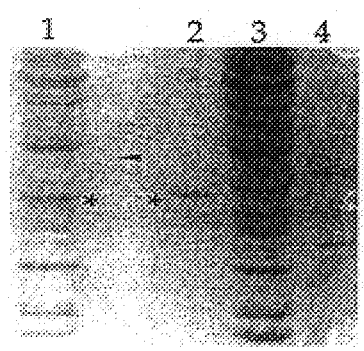
FIGS. 8a and 8b is a western blot analysis of the type B desaturase.
Figure 8B:
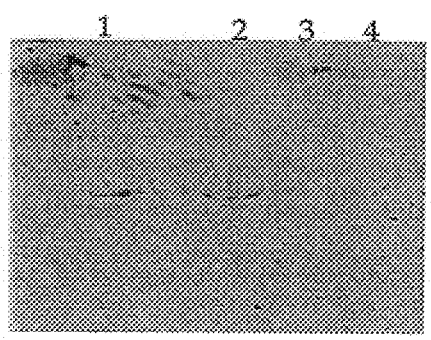
Figure 10:
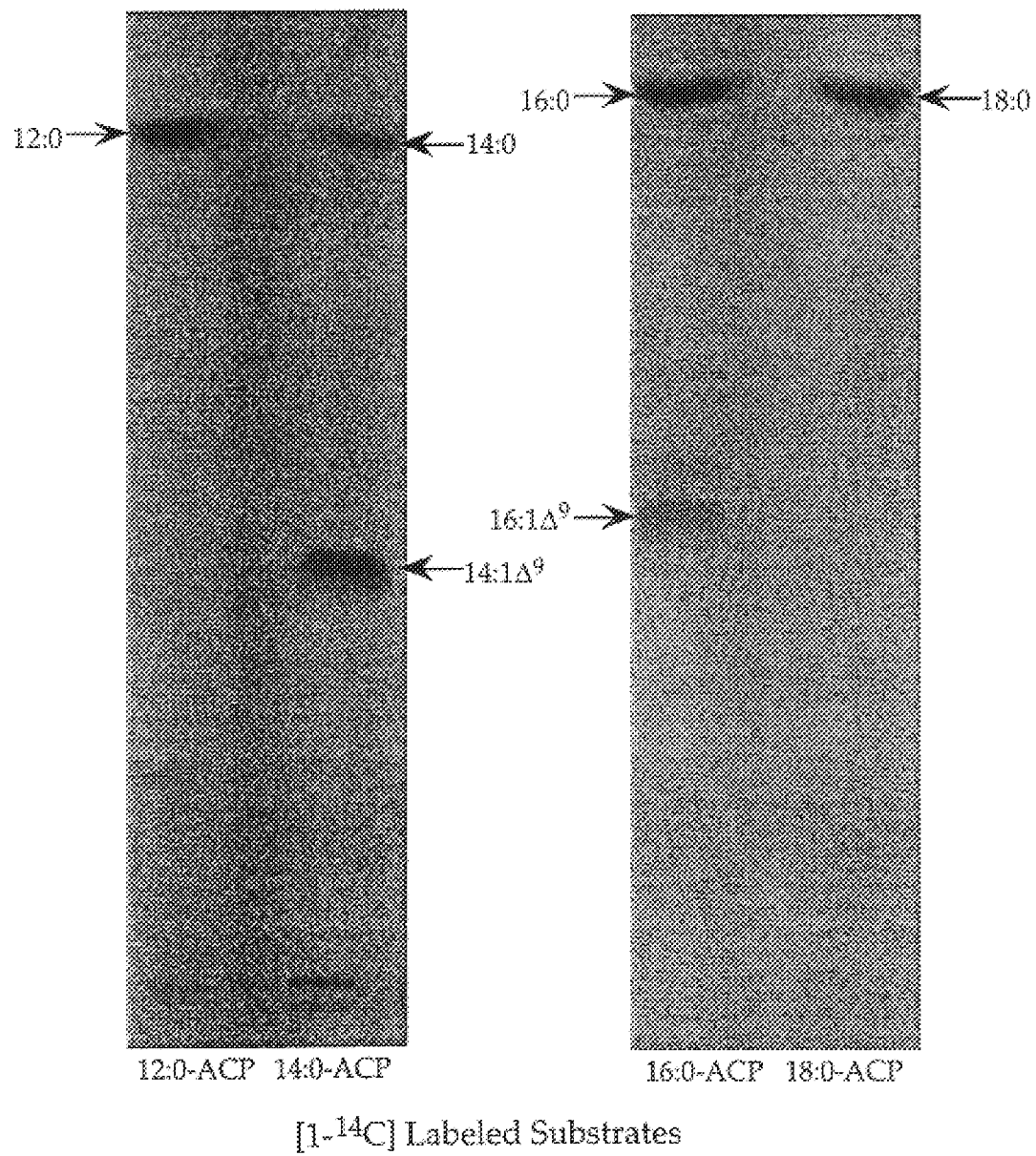
FIG. 10 is a substrate activity assay.
Figure 11:
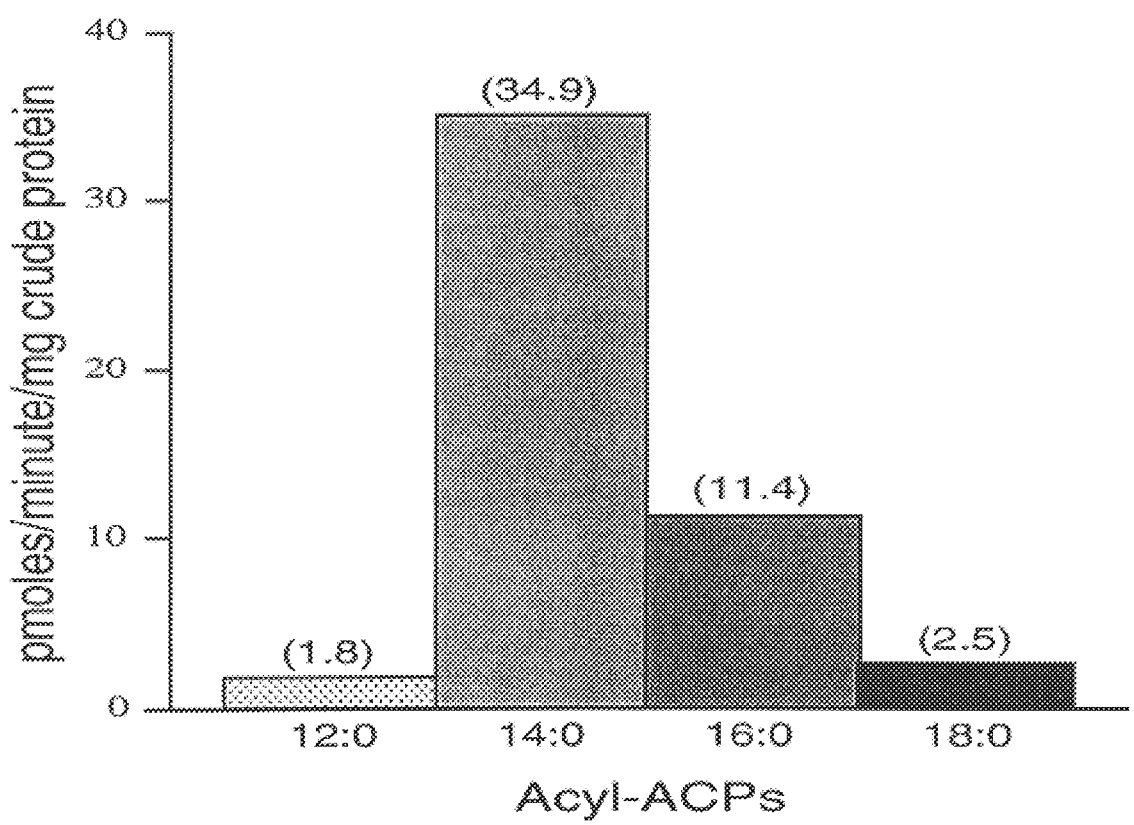
FIG. 11 is a quantification of acyl-ACP chain length specificity assay products.
Figure 13:
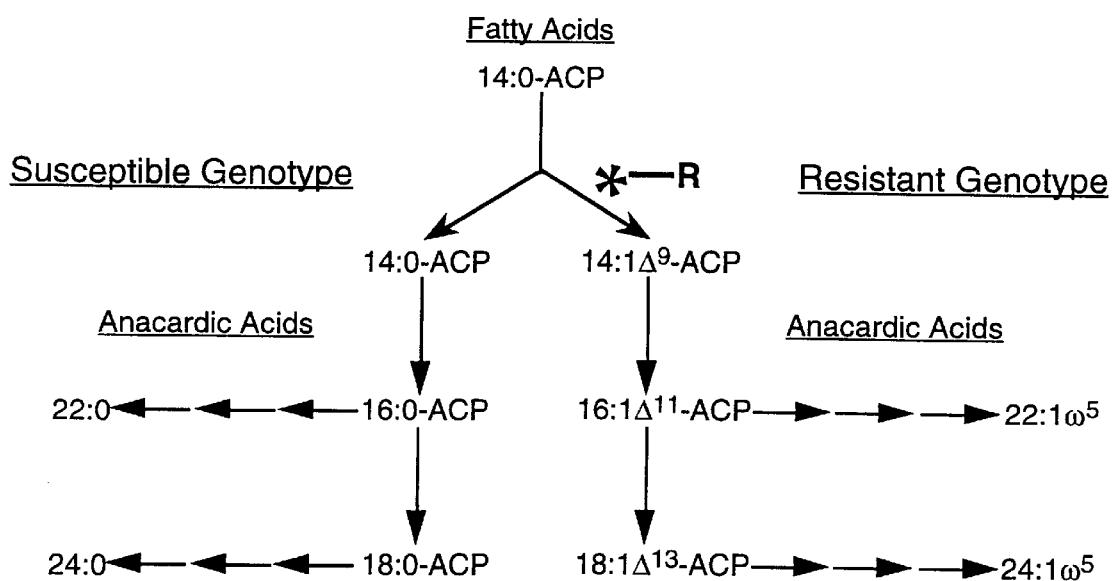
FIG. 13 is the proposed biosynthetic pathway model (starting from 14:0-ACP) of the 22:1 $\omega^5$ and 24:1 $\omega^5$ anacardic acids of the pest-resistant and pest-susceptible genotypes.

The present invention inheres in the isolation and characterization of a novel plant fatty acid desaturase cDNA that encodes a $\Delta^9$ 14:0-ACP desaturase. We demonstrate a close correlation between expression of this desaturase and the accumulation of 16:1 $\Delta^{11}$ and 18:1 $\Delta^{13}$ fatty acids and 22:1 $\omega^5$ and 24:1 $\omega^5$ anacardic acids, as well as to the pest-resistant genotype. Collectively, these data indicate that expression of the $\Delta^9$ 14:0-ACP desaturase is a critical factor for pest resistance.

The gene itself can also be introduced into other cells either to alter or to enhance the production of, as a single example, oil in those cells. For example, in some instances having a higher percentage of unsaturated fatty acids in an edible oil is commercially and agriculturally important. Oil-producing crops in which such an innovation is useful include (without limitation) soybeans, rapeseed, maize, sunflower, safflower, cotton, cuphea, peanut, coconut, and oil-palm. Similar engineering in nonedible oils, or oils not necessarily thought of as edible—such as pelargonium oil itself—also falls within the scope of this invention. Published and patented literature addressing this application includes, for example, U.S. Pat. No. 5,057,419 to Martin et al. The manner in which the gene is introduced into the plant host cell is not critical to the invention, and any manner of transformation may be employed such as electroporation, liposome fusion, DNA bombardments, etc. The gene and its expression products can also be used in connection with manufacturing methods known in the art, for example, in innovative processes for making specialty polymers such as NYLON and other methods in which unsaturated fatty acids are used as constituents or starting materials.

In order to clarify the development of the present invention, isolation of the gene from certain garden geraniums is addressed first, below.

All plant genotypes described originated from a resistant inbred (71-17-7) and susceptible inbred (71-10-1) that were maintained by vegetative propagation (Gerhold et al., 1984; Walters et al., 1990a). The resistant and susceptible inbreds were crossed reciprocally to produce $F_1$ hybrids. The $F_1$ plants were self-pollinated to produce the $F_2$ generation. Backcross generations were made by crossing the $F_1$ to each parental genotype. The backcross population resulting from the cross to the susceptible parent was used for molecular analysis. This backcross population was chemically characterized for the presence or absence of $\omega^5$ anacardic acids and grouped accordingly (Table 1). Chi square ($X^2$) analysis of this backcross generation for a 1 resistant:1 susceptible ratio (dominant heterozygote to the recessive homozygote) provides an acceptable fit (n=39, $X^2$=0.72, P≧0.46). Both parentals were self-pollinated to produce the inbred resistant line (88-51-10) and inbred susceptible line (88-50-10) used for molecular analysis. All tissue was harvested and frozen under liquid nitrogen. Samples were stored at −80° C. until used.

A geranium λ-Zap II cDNA library, prepared from RNA isolated from tissue rich in glandular trichomes (Clark, 1995) was screened under non-stringent conditions. The castor bean $\Delta^9$ 18:0-ACP desaturase cDNA clone (pRCD1) (Shanklin and Somerville, 1991) was used as a probe. To isolate the 1.6 kb cDNA free from the plasmid, 10 μg of pRCD1 was digested in a volume of 10 μl which includes 8–12 units EcoR I (Boehringer Mannheim), 50 mM tris-HCl (pH 7.5), 10 mM magnesium acetate, 100 mM NaCl, and 1 mM DTE (dithioerythritol). Samples were incubated for 2 hours at 37° C. Reactions were terminated by addition of 0.2 volumes 5x gel loading buffer (1.25% bromophenol blue, 1.25% xylene cyanol FF, 75% Ficoll [type 400], and 50 mM EDTA [ethylenediaminetetraacetic acid]. The 1.6 kb fragment was separated on a 0.7% agarose gel made in 1x TBE (90 mM Tris, 90 mM boric acid, 20 mM EDTA). To separate the fragments, the gel was run at 60 volts, for 3 hours. The 1.6 kb fragment was cut from the gel and placed in a microcentrifuge tube. To recover the fragment from the gel, the agarose block was minced in 500 μl phenol (buffered with TE [10 mM tris-HCl, 1 mM EDTA]) using a spatula. The sample was then frozen at −80° C. for 1 hour, thawed, minced again, and vortexed for ~30 seconds. The sample was microcentrifuged for 15 minutes, the aqueous phase was then transferred to a fresh tube and placed on ice. TE (200 μl) was added to the remaining phenol/agarose phase, and the sample was again minced, frozen, thawed, minced again, vortexed, and centrifuged, as above. The aqueous phase was added to that previously extracted. Next, the aqueous phase was extracted sequentially with 200 μl phenol:chloroform (1:1, v:v) and 200 μl chloroform. The DNA was recovered by precipitation with 0.1 volumes 3M sodium acetate (pH 5.2) and 2.5 volumes 95% ethanol. The precipitate was frozen on dry ice, then the DNA was pelleted by centrifugation for 15 minutes at 4° C. The pellet was rinsed with 70% ethanol, dried under vacuum in a Savant™ speed vac, then dissolved in 100 μl TE.

The 1.6 kb EcoR I, EcoR I full length castor bean cDNA fragment was radiolabeled with [$^{32}$P]α-dCTP (Amersham; 3,000 Ci (curies)/mmole; 10 mCi/ml) by a Prime-It II synthesis kit (Stratagene). The DNA fragment (30 ng) and random primers (9-mers) were denatured in a total volume of 34 μl by boiling in a water bath for 5 minutes. The denatured DNA was cooled to room temperature. The final reaction contained 34 mM tris-HCl (pH 7.5), 5 mM MgCl$_2$, 42 mM DTT (dithiothreitol), 50 μCi [$^{32}$P]α-dCTP, and 5 units Klenow fragment DNA polymerase. The reaction was incubated for 10 minutes at 37° C. and terminated by adding 0.2 volumes 5x stop buffer. The radiolabeled probe was purified by a spin column.

Replicate filters of five 150 mm plates, each containing ~35,000 pfu (plaque forming units) were screened. *Esherichia coli* cells (XL1) were grown overnight in LB medium (10 g bacto-tryptone, 5 g bacto-yeast, and 10 g NaCl per liter [pH adjusted to 7.0 with NaOH]) containing 0.2% maltose. Cells were collected by centrifugation in a table top centrifuge for 5 minutes. The cells were resuspended in 10 mM $MgSO_4$. The cells were then inoculated with a geranium λ-Zap II cDNA library (Clark, 1995). The cells (300 μl) were added to the phage, then incubated for 15 minutes at 37° C. To plate the infected cells, 6.5 ml 2X YT medium (16 g bacto-tryptone, 10 g bacto-yeast, and 5 g NaCl per liter, pH adjusted to 7.0 with NaOH) containing 0.75% agarose (maintained at 50° C.) was added to the mixture, then gently mixed. The mixture of cells were poured onto 150 mm LB 1.5% agar plates. After the mixture solidified, the plates were inverted and incubated at 37° C. for 12 hours.

Replicate plaque lifts (A and B) were taken from each plate. The nitrocellulose filters (BA-S NC, Schleicher & Schuell, Keene, N. H.) were placed directly onto the plates containing the phage plaques. The "A" lifts were placed on the plates for 5 minutes and the "B" lifts were placed on the plates for 10 minutes. After the filters were taken removed from the plates, they were soaked (DNA side up) on 3MM Whatman filter paper soaked with 0.5N NaOH, 1.5M NaCl for 3 minutes. The filters were then transferred to a solution of 0.5M tris-HCl (8.0), 1.5M NaCl, and finally a solution of 2X SSPE (100 mM NaCl, 100 mM $NaH_2PO_4.H_2O$, 2.5 mM EDTA). The filters were air dried, then baked at 80° C. to covalently attach the DNA.

The filters were prehybridized (3 hours) and hybridized (24 hours) at 42° C. in a solution of 25% formamide, 5X SSPE (250 mM NaCl, 250 mM $NaH_2PO_4.H_2O$, and 6.5 mM EDTA), 5X Denhardt's (0.2% ficoll, 0.2% polyvinylpyrolidone, and 0.2% bovine senum albumin [BSA]), 100 μg/ml denatured salmon sperm DNA, 1% SDS (sodium dodecyl sulfate) (Sambrook et al., 1989). The filters were washed in 25% formamide, 5X SSPE, 0.5% SDS for 15 minutes at 42° C. four times. A final wash in 5X SSPE, 0.5% SDS was at 50° C. for 1 hour. Positive plaques were identified following autoradiography (Kodak, XAR film) and each positive plaque was rescreened through two further rounds to isolate a single pure bacteriaphage.

After all positive clones were purified, the plasmid (pBluescript, SK⁻, Stratagene) was excised. Two *E. coli* lines (XL1 and Solr™) were used to recover the plasmids. Overnight cultures were grown for each cell line. The XL1 cells were grown at 37° C. in LB while the Solr™ cells were grown in LB supplemented with 50 μg/ml kanamycin. The cells were collected by centrifugation for 5 minutes in a table top centrifuge, then resuspended in 10 mM $MgSO_4$. In sterile 5 ml snap cap tubes, 200 μl XL1 cells, 100 μl purified phage stock and 1 μl Exassist™ helper phage were gently mixed together. The helper phage functions to excise the bluescript phagemid from the λ-phage containing recombinant cDNA. The cells were then incubated at 37° C. for 15 minutes. Then 3 ml 2X YT was added, and the samples were incubated at 37° C. for 2 hours with constant agitation. The samples were then heated to 70° C. for 20 minutes and centrifuged for 5 minutes on a table top centrifuge. The supernatant (filamentous phage solution) was transferred to a fresh tube. The filamentous phage (1 μl) was then added to the Solr™ cells (200 μl) and incubated at 37° C. for 15 minutes. Rescued plasmids were identified by plating aliquots of the infected Solr™ cells onto 1.5% agar LB plates supplemented with 100 μg/ml carbenicillin.

Purified plasmid DNA was sequenced to identify possible desaturase-like clones. Plasmid inserts were manually sequenced by dideoxy chain termination with the use of Sequenase Version 2.0 kit (United States Biochemical) (Sambrook et al., 1989). For all sequencing reactions, 3–4 μg of plasmid DNA was denatured with 0.2N NaOH, 20 mM EDTA in a 20 μl volume. The samples were incubated for 5 minutes at room temperature, then the denatured DNA was precipitated by the addition of 0.4 volumes 5M ammonium acetate and 3.6 volumes 95% ethanol. The samples were frozen on dry ice, then the DNA was pelleted by centrifugation for 15 minutes at 4° C. The pellets were rinsed with 70% ethanol, then air dried. The DNA pellets were resuspended in a solution containing 1 pmole sequencing primer, 50 mM tris-HCl (pH 7.5), 25 mM $MgCl_2$, 62.5 mM NaCl, then heated to 65° C. for ~2 minutes and allowed to slowly cool to 30° C. Synthesized DNA was labeled and chain elongation terminated at room temperature for 5 minutes. Reactions contained the additional components: 7.5 μM dGTP, 7.5 μM dCTP, 7.5 μM dTTP, 7 mM DTT, 1.5 units Sequenase, and 5 μCi [$^{35}$S]α-dATP. Chain termination was accomplished by transferring 3.5 μl of the reaction to each one of four tubes for each ddNTP (dideoxy NTP). The ddGTP termination tube included 8 μM dATP, dCTP, dTTP and ddGTP, the ddATP termination tube included 8 μM dCTP, dTTP, dGTP, and ddATP, the ddCTP termination tube contained 8 μM dTTP, dGTP, dATP, and ddCTP, and the ddTTP termination tube contained 8 μM dGTP, dATP, dCTP and ddTTP. Gel loading buffer was added to the samples to a final concentration of 38% formamide, 8 mM EDTA, 0.02% bromophenol blue, and 0.02% xylene cyanol FF. Samples were stored at −20° C.

Sequence reaction fragments were separated on a 6% denaturing polyacrylamide gel (8.3M urea, 1× TBE, 6% polyacrylamide [containing 0.3% bis-acrylamide], 0.001% ammonium persulfate and 1.3 mM TEMED [N,N,N',N'-tetramethylethylenediamine]). The gel was electrophoresed with watts limiting at 60. Thus, the voltage and mAMPs were increased to maintain a constant 60 watts. Gels were generally run for 3.5 hours for the first sample and 2.5–3 hours for the second identical sample. Therefore, the first sample was electrophoresed between 6–6.5 hours. After the gel was run, it was soaked in a solution of 10% methanol and 10% acetic acid for 20 minutes, then transferred to Whatman 3MM paper, covered with plastic wrap, and dried on a acrylamide gel drier for 1 hour at 80° C. The dried gel was then exposed on Kodak XAR film. Sequence homology was determined using the BestFit, PileUp, and TFASTA programs of GCG (Genetics Computer Group, Madison, Wis.) analysis package.

RNA was isolated from geranium tissues (leaves with intact trichomes, pedicel tissue stripped of trichomes, and trichomes taken from the pedicel tissue). Total RNA (30 μg) was electrophoresed on a denaturing agarose gel containing 1.4% agarose, 1× MOPS (2 mM 3-[N-morpholino] propane sulfonic acid, 0.5 mM sodium acetate, 0.1 mM EDTA), 6% formaldehyde, and 0.4 mg/ml ethidium bromide at 24 volts for 24 hours. RNA was transferred to nylon membrane (GeneScreen Plus, DuPont) by capillary action (Sambrook et al., 1989). Whatman filter paper (14 pieces, cut to the gel measurements) was soaked in a reservoir of 20X SSPE. The RNA gel was placed onto of the soaked filter paper, and the nylon membrane was placed on the top to the RNA gel. Next, 3 pieces of Whatman 3MM filter paper, soaked in 10X SSPE were placed on top of the nylon membrane. A stack of paper towels was placed on top of the 10X SSPE soaked filter paper to draw the 20X SSPE through the gel and membrane. An ~300 g weight was placed on top of the paper towels to ensure constant contact. The gel was blotted overnight. After blotting, the membrane was rinsed with 2X SSPE, air dried, then baked at 80° C. for 2 hours to fix the RNA to the membrane. The RNA gel blot was probed with the 3' untranslated region (Hinf I/EcoR I, 3' fragment) of the geranium type B clone. The 212 bp (base pair) Hinf I, EcoR I fragment from the plasmid pPXH-9 which contained the type B desaturase clone was isolated in two steps. First, a 3' 522 bp Hind III, EcoR I fragment containing the Hinf I, EcoR I fragment was isolated by digesting 1 µg pPXH-B with 6–9 units Hind III (Promega) and 6–9 units EcoR I (Boehringer Mannheim) in a total volume of 15 µl containing 50 mM tris-HCl, 10 mM magnesium acetate, 100 mM NaCl, and 1 mM DTE for 2 hours at 37° C. The digested fragments were separated, and the 522 bp fragment was recovered. The Hind III, EcoR I fragment was then digested with 8–12 units Hinf I (Promega) in a total volume of 20 µl containing 6 mM tris-HCl (pH 7.5), 6 mM $MgCl_2$, 50 mM NaCl, and 1 mM DTT for 22 hours at 37° C. The digested fragments were separated by electrophoresis, and the 212 Hinf I, EcoR I fragment was recovered. A radioactive probe was made by labeling the Hinf I, EcoR I fragment with [$^{32}P$]α-dCTP with the Prime-It II® synthesis kit (Stratagene).

The blot was prehybridized at 65° C. for 3 hours in a solution of 10% dextran sulfate, 1% SDS, and 1M NaCl. After prehybridization was performed, 1 mg sheared salmon sperm DNA was added to the probe, boiled for 5 minutes, then cooled immediately on ice. The probe was then added to the prehybridization solution. Hybridization was for 15 hours at 68° C.

After hybridization, the membrane was washed twice for 5 minutes at room temperature in 2X SSPE, 1% SDS followed by a single wash for 30 minutes at 65° C. in 1X SSPE, 0.1% SDS and one wash for 15 minutes at 68° C. in 0.5X SSPE, 0.1% SDS. Expression of the gene was analyzed with autoradiography (Kodak XAR-5 film) and radioactive signal was quantified with a PhosphorImager 445 SI (Molecular Dynamics). The blot was exposed on the PhosphorImager cassette for 25.5 hours before quantification. The blot was then stripped of the labeled probe by washing in 0.1X SSPE, 0.1% SDS at 100° C. until no signal could be detected.

To verify RNA loading, the *Arabidopsis thaliana* 18S ribosomal DNA 0.4 kb EcoR I, Hind III fragment (from plasmid SBG10T79, Arabidopsis Stock Center, Ohio State University) was used to probe the RNA gel blot. The plasmid was digested with Hind III, EcoR I (as described above). The fragments were separated by agarose gel electrophoresis and then purified. Hybridization was as described above. To express the type B clone in *E. coli*, the cDNA corresponding to the mature peptide was cloned into the pET3d vector (Novagen). PCR (polymerase chain reaction) primers were designed to allow amplification of the mature peptide by synthesis of oligonucleotides encoding the amino acids denoted in bold in FIG. 3.3. A Nco-I site was incorporated into the upstream primer and a Bgl II site was incorporated into the downstream primer to allow directional cloning into the pET3d vector. The primers are: (1) 5'-ggggccatggcttctacttccattt-3' (corresponding to amino acids ASTSI starting at position 18) and (2) 5'-ggggagatctcactagactttctat-3' (corresponding to amino acids DRKV starting at position 366).

PCR reactions were performed using a DNA thermocycler (Perkin Elmer Cetus, Norwalk, Conn.). PCR reactions were carried out in a volume of 100 µl containing 10 ng pPXH-9, 0.5 µM of each primer, 50 µM dNTPs, 1 unit Taq DNA polymerase (Boehringer Mannheim, Indianapolis, Ind.) 10 mM tris-HCl (pH 8.3), 50 mM potassium chloride, and 0.05% nonidet P-40. Each sample was covered with 60 µl mineral oil to prevent evaporation during cycling. Reactions were carried out for 35 total cycles. Each cycle had a denaturation step at 94° C. for 30 seconds followed by an annealing step at 55° C. for 30 seconds and a synthesis step at 72° C. for 90 seconds. After reactions were complete, the 100 µl volume was purified by phenol chloroform extraction. The PCR mixture, excluding the mineral oil, was transferred to a fresh tube. Phenol-chloroform 1:1 (v:v) (100 µl) was added to the tube, then the sample was mixed by vortexing ~30 seconds. The sample was centrifuged for 10 minutes at 4° C., and the aqueous phase was transferred to a fresh tube. The extraction was repeated using 100 µl chloroform. The DNA was precipitated with addition of 0.1 volumes 3M sodium acetate and 2.5 volumes 95% ethanol. The DNA was pelleted by freezing on dry ice, and centrifuging for 15 minutes. The supernatant was discarded, and the pellets were rinsed with 70% ethanol, then air dried. The PCR product was digested in a 100 µl volume containing 30 units Nco I (Boehringer Mannheim, Indianapolis, Ind.), 30 units Bgl II (Promega), 6 mM tris-HCl (pH 7.9), 6 mM MgCl, 150 mM NaCl, and 1 mM DTT. The expression plasmid, pET3d (5 µg) was digested in a 10 µl volume containing 8–12 units Nco I (Boehringer Mannheim, Indianapolis, Ind.) and 8–12 units BamH I (Promega), 10 mM tris-HCl (pH 7.9), 10 mM $MgCl_2$, 50 mM NaCl, and 1 mM DTT. Digests were conducted for 10 hours at 37° C. The resulting fragments were separated by agarose gel electrophoresis and purified.

The PCR fragment was ligated into pET3d in a 10 µl volume containing 25 ng digested PCR fragment and 50 ng digested pET3d vector, 1 unit T4 ligase (Boehringer Mannheim, Indianapolis, Ind.), 66 mM tris-HCl (pH 7.5), 0.5 mM $MgCl_2$, 1 mM DTE, and 1 mM ATP. Ligations were performed at room temperature for 2 hours.

The ligations were then transformed to the *E. coli* DH5α cell line. An aliquot of the ligation reaction (5 µl) was added to 80 µl electroporation competent DH5α cells in an electroporation cuvette (BTX, Inc., San Diego, Calif.). The electroporation cuvette was placed in the electroporator and at 1500 volts, 50 mAmps, and 50 watts for 30 seconds. The power was discharged and the transformation mixture was immediately transferred to a flask containing 10 ml SOC (20 g bactotryptone, 5 g bacto-yeast extract, 0.5 g NaCl, and 3.6 g glucose per liter). The sample was incubated at 37° C. for 1 hour with moderate shaking. The transformed cells were collected by centrifugation in a table top centrifuge for 5 minutes, and resuspended in the residual media. To select for positive transformants, 100 µl transformed cells were plated onto 1.5% agar LB plates supplemented with 100 µg/ml carbenicillin. Plates were inverted and incubated overnight at 37° C. Bacterial colonies that grew were selected for further analyses.

Plasmid DNA from each bacterial colony was digested with BamH I, Pst I to determine the identity of the clone, as the type B clone contains an internal 315 bp BamH I, Pst I fragment. The digests were in 15 µl containing 6–9 units BamH I (Promega), 6–9 units Pst I (Promega), 6 mM tris-HCl (pH 7.5), 6 mM $MgCl_2$, 100 mM NaCl, and 1 mM DTT, for 1 hour at 37° C. The fragments were separated on a 1.2% agarose gel run in 1X TBE. After identifying a positive clone, the plasmid was electroporated (as described above) into a modified *E. coli* expression line. The cell line used for this transformation, BL21(DE3), had been modified for expression of plant acyl-ACP desaturases by co-expression of an *Arabidopsis thaliana* ferredoxin gene (Cahoon et al., 1996). By cloning the Arabidopsis ferredoxin gene into the pACYC vector (New England Biolabs), expression of this gene was placed under control of the T7 RNA polymerase promoter. Thus induction with IPTG (isopropyl β-D-thiogalactopyranoside) controls the expression of the desaturase and the ferredoxin genes. The expression of the Arabidopsis ferredoxin gene is important, as the level or structure of E. coli ferredoxin appear to be adequate for a plant fatty acid desaturase (Cahoon et al., 1996). The expression of the Arabidopsis ferredoxin gene increases the level of available ferredoxin. The resulting expression line was called pPXH-B.

To determine if any the putative desaturase encoded by pPXH-B cross-reacts with the antibody generated against the avacado $\Delta^9$ 18:0-ACP desaturase, western blot analysis was used. Cultures of pPXH-B were started in 3 ml LB, supplemented with 100 µg/ml carbenicillin and 34 µg/ml chloramphenicol and grown overnight at 37° C. A 25 ml LB (100 µg/ml carbenicillin, 34 µg/ml chloramphenicol) culture was inoculated with 300 µl of the pPXH-B overnight culture. The cells were grown at 37° C. with moderate agitation until an O.D.(optical density)$_{600}$=0.4. Expression of the type B desaturase was then induced by addition IPTG to 0.4 mM, and the cells were incubated an additional 6 hours, at 20° C. with moderate agitation.

The cells were collected by centrifugation at 6.5K rpm for 5 minutes at 4° C. GA-20 rotor). The cells were resuspended in 0.1 culture volume of 45 mM tris (pH 7.6), 2 mM EDTA, and 10% glycerol. Freshly prepared lysozyme (0.25 mg in 50 mM tris, 2 mM EDTA) and 0.1 volumes 1% triton X-100 was added to lyse the cells. Lysis was conducted at 30° C. for 15 minutes. After lysis, the DNA was sheared by sonication (250/450 Sonifier, Branson Ultrasonics Corporation, Danbury, Conn.) with 2–3 moderate intensity pulsed (10 seconds each). Cellular debris and insoluble proteins were pelleted by centrifugation at 10K for 15 minutes at 4° C. Samples of the supernatant (containing the soluble protein fraction) were aliquoted into 1.5 ml microcentrifuge tubes. Each sample was frozen under liquid nitrogen and stored at −80° C.

Equal volumes of each protein extract were separated by PAGE electrophoresis. A 4% stacking gel (125 mM Tris-HCl [pH 6.8], 0.1% SDS, 4% polyacrylamide [containing 0.3% bis-acrylamide], 0.05% ammonium persulfate, 1.3 mM TEMED) and a 12% separating gel (375 mM Tris-HCl [pH 8.8], 0.1% SDS, 12% polyacrylamide [containing 0.3% bis-acylamide], 0.05% ammonium persulfate, 1.3 mM TEMED).

The proteins were electroblotted onto nitrocellulose membrane (BA-S NC, Schleicher & Schuell) using a BioRad mini-gel electro-blotting apparatus. The blot was conducted in 25 mM Tris-HCl, 192 mM glycine and 20% methanol. The transfer was for 3 hours at 100 volts. After transfer, the blot was stained with 0.1% Ponceau-S in 5% acetic acid, and protein positions were marked with a soft lead pencil on the edge of the membrane. The gel was stained with coomassie blue in a 40% methanol, 10% acetic acid solution so that the protein positions marked on the membrane could be associated with size markers.

After protein transfer, the western blot was blocked in 10 mM Tris-HCl 0.9% NaCl, 0.2% NaN$_3$, 1% BSA (fraction V). The primary antibody ($\Delta^9$ desaturase antibody) obtained from Dr. John Shanklin was diluted 100 fold in 20 mM Tris-HCl (pH 7.4) containing 3% BSA (fraction V). The diluted antibody (1 ml) was added to 10 ml blocking solution, then incubated with the membrane for 1.5 hours. The membrane was then rinsed with dH$_2$O, then washed with 10 mM Tris-HCl, 0.9% NaCl, 0.02% NaN$_3$, 0.1% TritonX-100, 0.05% SDS, on 0.1% BSA (fraction V). The membrane was then rinsed rapidly 3 times with dH$_2$O. The wash/rinse cycle was repeated a total of 3 times. The membrane was then incubated in blocking solution for 10 minutes to reduce background. The secondary antibody (anti-rabbit-Ig G, Sigma Chemical Company) was prepared in 5 ml blocking solution at a 1:1000 dilution. The membrane was incubated with the secondary antibody for 1.5 hours. The western was rinsed and washed as described above. The membrane was rinsed in blocking solution, then placed on parafilm. Development buffer (5 ml) containing 90 mM Tris-HCl (pH 8.8), 90 mM NaCl, 4.5 mM MgCl$_2$, 1 mg p-nitro blue tetrazolium, and 0.5 mg N,N-dimethylformimide. Reactions were terminated by transferring the membrane to dH$_2$O when reactions were visible.

The geranium type B clone (pPXH-B) was expressed in E. coli as described (Cahoon et al., 1996). Control cells BL21 (DE3) were grown in parallel to the pPXH-B cell line. Inoculations of pPXH-B were made in 3 ml LB supplemented with 100 µg/ml carbenicillin and 34 µg/ml chloramphenicol, whereas BL21(DE3) was in LB with no antibiotics. Cultures were grown at 37° C. with constant agitation until an O.D.$_{600}$=1. Next, 25 ml LB supplemented with 100 µg/ml carbenicillin and 34 µg/ml chloramphenicol was inoculated with 150 µl of the 3 ml pPXH-B culture, and 25 ml LB was inoculated with 150 µl of the 3 ml BL21(DE3) culture. To induce expression of the desaturase, IPTG was added to a final concentration of 0.1 mM. The cultures were grown overnight at 20° C. with constant agitation. The cells were collected by centrifugation at 3K rpm for 5 minutes at 4° C. (JA-10 rotor).

Transesterification reactions were carried out by the addition of 0.5 ml 12% borontriflouride in methanol (Supelco) to the pellets. Glass reaction vials were sealed with Teflon lined caps. The reaction was carried out at 100° C. for 1 hour. After transesterification, 1 volume of dH$_2$O and 2 volumes of hexane were added. The samples were mixed vigorously, then centrifuged at 3K rpm in a table top centrifuge. The hexane layer was transferred to a fresh tube. The remaining aqueous phase was extracted again with 2 volumes of hexane, mixed vigorously, centrifuged, and the recovered hexane was added to the previous extraction. The hexane was evaporated under a stream of nitrogen. The fatty acid methyl esters (FAMEs) were dissolved in 50 µl hexane.

The FAMEs were analyzed by gas chromatography with a Hewlett Packard 5890 GC equipped with a 30 m RTX2330 0.25µ capillary column (Restek) with helium as the carrier gas at 8 ml/minute. Injector and detector temperatures were 300° C. The initial temperature was 40° C. with a 4 minute hold time. The rate of ramp was 6° C./minute to a final temperature of 300° C. at a hold time of 7.67 minutes. Dimethyl disulfide adducts of fatty acid methyl esters were prepared (Yamamoto et al., 1991) by mixing the FAMEs (in 50 µl hexane) with 50 µl dimethyldisulfide and 50 µl iodine solution (60 mg iodine in 1 ml diethylether). The reaction vial was sealed with a cap lined with teflon, and allowed to incubate overnight at 40° C.

Next, 200 µl hexane was added. The iodine was removed by treatment with 100 µl sodium thiosulfate (5% in dH$_2$O). The sample was hexane extracted (described above), and the hexane was evaporated under a stream of nitrogen, then the sample was redissolved in 50 µl hexane.

Methyl esters of fatty acids and their dimethyl disulfide derivatives were identified by mass spectral analysis with a Hewlett Packard 5890 Series II GC equipped with a 30M 0.53μ capillary SE-54 column (Alltech) and a Hewlett Packard 5971 mass selective detector with helium as the carrier gas at 8 ml/minute. Injector and detector temperatures were 300° C. The initial temperature was 40° C. with a 4 minute hold time. The rate of ramp was 6° C./minute to a final temperature of 300° C. at a hold time of 7.67 minutes.

To assess the activity of the type B desaturase, in vitro reactions were performed using crude protein extracts of pPXH-B (Cahoon et al., 1994b) as described in Western Blot Analysis above. Total crude protein concentration was determined using the BCA protein assay (Pierce Chemical Company). Protein samples (100 μl) were quantified by the addition of 2 ml assay reagent (50:1 ratio, reagent A to reagent B; the final solution contains copper sulfate, sodium carbonate, sodium bicarbonate, BCA reagent [bicinchoninic acid], sodium tartrate and NaOH). The samples were mixed, then incubated at 37° C. for 30 minutes. Absorbance readings were taken at 562 nm and compared with a BSA standard curve for quantitative estimates.

The in vitro desaturase assay has been described (Cahoon et al., 1994b). Reactions were conducted in a total volume of 150 μl. Briefly, 4 separate reactions, each containing 3.3 mM ascorbic acid, 0.67 mM DTT, 800 units catalase, 5 μg BSA (bovine serum albumin, fraction V), 20 μg ferredoxin, 0.8 units ferredoxin nucleotide reductase, 1.25 mM NADPH, 33.3 mM PIPES (piperazine-N, N'-bis [2-ethanesulfonic acid] 1,4-piperazinediethanesulfonic acid), 81 μg crude pPXH-B protein extract, and 500 μM cerulenin (to inhibit $E.$ $coli$ fatty acid elongation enzymes) were conducted (Magnuson et al., 1993). Each reaction contained 124 pmoles of a single substrate. Four acyl-ACP substrates [1-$^{14}$C] 12:0-, 14:0-, 16:0-, and 18:0-ACP, synthesized as described (Rock and Garwin, 1979), were tested. Reactions were conducted for 30 minutes at room temperature. Reactions were terminated by addition of NaOH to a final concentration of 2N. The samples were mixed, incubated at 95° C. for 1 hour, then $H_2SO_4$ was added to a final concentration of 1M.

Samples were extracted with hexane as described above. Before making FAMEs, non $^{14}$C-labeled fatty acid standards were added to the samples for localization of FAMEs and reaction products on TLC (thin layer chromatography). The following additions had been made to each reaction: 25 μg 14:1$\Delta^9$ and 25 μg 16:1$\Delta^9$ were added to the [1-$^{14}$C] 12:0 reaction products, 25 μg 14:1$\Delta^9$ and 25 μg 16:1$\Delta^{11}$ were added to the [1-$^{14}$C] 14:0 reaction products, 25 μg 16:1$\Delta^9$ and 25 μg 16:1$\Delta^{11}$ were added to the [1-$^{14}$C] 16:0 reaction products, and 25 μg 18:1$\Delta^9$ and 25 μg 18:1$\Delta^{13}$ were added to the [1-$^{14}$C] 16:0 reaction products. FAMEs were then made as described above.

Samples were analyzed on TLC plates treated with 15% $AgNO_3$ and toluene as the mobile phase (Cahoon and Ohlrogge, 1994). TLC plates (5×20 cm Kieselgel 60 E, Merk Chemical Co.) were soaked in a solution of 15% $AgNO_3$ (in acetonitrile) for at least 10 minutes. The plates were air dried, then stored in the dark overnight to minimize photo oxidation of the $AgNO_3$. FAMEs (in 50 μl hexane) were transferred onto the plate, approximately 3.8 cm from the bottom. Transfer was accomplished by drawing small aliquots of the sample into a capillary tube, then dotting the sample onto the plate. The hexane was evaporated before dotting additional sample. This process was repeated until the entire sample was dotted onto the TLC plate. The TLC plates were developed with toluene three times in chromatography tanks (Supelco). The first development was to a height of 6.7 cm, the second was 13 cm, and the final was to within 1.25 cm of the top. The plates were then put under film (Kodak, XAR). The radioactivity was quantified by an Ambis 400 TLC plate reader AMBIS Core Software version 4.0 at a scan time of 15 hours. Detected signal (counts per minute) of unsaturated product to unreacted saturated substrate was used to determine the percent unsaturated product. The mole quantity of unsaturated product was determined by multiplying the percent unsaturated product by 124 pmoles.

Double bond placement was verified by a modified in vitro assay. In vitro reactions were as described above except the reactions were scaled-up 20-fold, incubation time was 40 minutes, and 15:0-ACP (1.5 μM) was used as the substrate. Reactions were terminated, derivitized and extracted as described above and dimethyl disulfide derivatives were prepared and analyzed by GC/MS as described earlier.

The $\Delta^9$ 18:0-ACP desaturase gene exists as part of a gene family in $Thunbergia$ $alata$, where three independent $\Delta^9$ 18:0-ACP desaturase-like genes have been isolated (Cahoon et al., 1994a). In addition, two novel acyl-ACP desaturases ($\Delta^4$ 16:0-ACP and $\Delta^6$ 16:0-ACP) with high homology to the $\Delta^9$ 18:0-ACP desaturase have been identified (Cahoon et al., 1994b; Cahoon et al., 1992). These desaturases recognize a shorter acyl chain and place double bonds at distinct positions. Hence, we reasoned that a variant acyl-ACP desaturase could be involved in the production of 16:1 $\Delta^{11}$ and 18:1 $\Delta^{13}$ found in the pest-resistant genotype of geranium.

When a castor bean $\Delta^9$ 18:0-ACP desaturase probe was used in geranium Southern blot analysis under low stringency conditions, multiple signals were detected, suggesting the presence of a gene family FIG. 3.4). To identify acyl-ACP desaturase clones that may be involved in pest resistance, a trichome enriched cDNA library was screened with the castor bean $\Delta^9$ 18:0-ACP desaturase probe. Two classes of clones were isolated and designated type A and type B based on restriction endonuclease analysis FIG. 3.5).

Type A clone was sequenced and the longest open reading frame had 96% amino acid similarity to the castor bean $\Delta^9$ 18:0-ACP desaturase. Hence, the type A clone likely represents a $\Delta^9$ 18:0-ACP desaturase homologue. In contrast, the type B clone was sequenced and has an open reading frame with 79% amino acid similarity to the castor bean $\Delta^9$ 18:0-ACP desaturase, 73% to the coriander $\Delta^4$16:0-ACP, and 75% to the Thunbergia $\Delta^6$ 16:0-ACP suggesting it may represent a novel desaturase. More detailed studies focused on the type B clone.

FIG. 3.3 shows the deduced amino acid sequence of the type B clone. The ATG (nucleotides 8–10) is likely the initiation codon because a G is found at position +4, consistent with the consensus for plant translation initiation sites (Lutcke et al., 1987). Though there is divergence between the transit peptides of different acyl-ACP desaturases, there is homology between the transit peptide cleavage sites (Cahoon et al., 1994b). Such a consensus cleavage site is found between residues 18 and 19 (Gavel and von Heijne, 1990). This indicates that either the type B clone has a very short transit peptide, or that the clone is truncated at the 5' end. In either case, the identification of a conserved cleavage site suggested that the entire mature peptide coding sequence is represented in this type B clone.

Expression of the type B gene was analyzed to determine if it followed the expected pattern for pest resistance. FIG. 3.6 shows the type B gene was expressed only in RNA from trichomes of the resistant genotype (compare lanes 1 and 2 to 5 and 6). All other tissues analyzed (pest-resistant leaves and pedicels; pest-susceptible trichomes, leaves and pedicels) displayed no significant type B expression levels.

Phosphorimager quantification (Table 2) indicated that there is at least 20-fold greater expression in the resistant trichomes compared to the susceptible trichomes. Expression of the type B gene in the resistant genotype trichomes was consistent with the production of the novel fatty acids (16:1$\Delta^{11}$ and 18:1$\Delta^{13}$) as well as the $\omega^5$ anacardic acids (22:1 $\omega^5$ and 24:1 $\omega^5$). In addition, type B gene expression was at least 31-fold greater in trichomes of the resistant genotype than in all other "nontrichome" tissues (Table 2). Expression in trichomes from homozygous plants was found to be 1.9 fold higher than expression in trichomes from heterozygous plants (FIG. 3.6 A, lanes 1 and 2; Table 2). This pattern is consistent with the effects predicted for two copies of the dominant allele in the homozygous plants compared to one copy of the dominant allele in the heterozygous plants.

The type B gene was placed under the control of an inducible promoter in E. coli in order to determine if its product functions as a desaturase. Upon induction, a protein of approximately 39 kDa was produced (FIG. 3.7). This peptide has a similar size to that predicted to be encoded by the cDNA sequence. In addition, this protein cross-reacts with antibodies generated against the avocado $\Delta^9$ 18:0-ACP desaturase, indicating that the 39 kDa protein shares a structural similarity (FIG. 3.8).

E. coli fatty acids were analyzed to determine if the 39 kDa type B polypeptide had desaturase activity. The fatty acid profiles of the E. coli cell line BL21(DE3) grown with expression of the type B clone were compared to the fatty acid profile of the native cell line. In controls, the only unsaturated moieties detected were methyl esters of palmitoleic acid (16:1 $\Delta^9$) and cis-vaccenic acid (18:1$\Delta^{11}$) (FIG. 3.9). When the 39 kDa, type B gene product was expressed, two new fatty acids, identified as methyl esters of 16:1$\Delta^{11}$ and 18:1$\Delta^{13}$, were detected (FIG. 3.9). These could either result from a $\Delta^{11}$ 16:0 desaturation reaction or from desaturation of a shorter acyl chain and subsequent elongation to 16:1$\Delta^{11}$ and 18:1$\Delta^{13}$. In order to distinguish between these two possibilities, chain length specificity of the type B desaturase was assessed.

The chain length specificity of the type B clone was determined with in vitro assays and [1-$^{14}$C] 12:0-, 14:0-, 16:0- and 18:0-ACP substrates (Rock and Garwin, 1979). Assays contained crude E. coli protein extract and cerulenin (500 $\mu$M) to inhibit the E. coli fatty acid elongation enzymes (Cahoon et al., 1994b; Magnuson et al., 1993). Methyl esters were made and separated by TLC (FIG. 3.10). The unreacted substrate and unsaturated products were quantified for each reaction using a TLC plate reader. FIG. 3.11 shows that the type B desaturase was three fold more active with [1-$^{14}$C]-14:0-ACP than with [1-$^{14}$C]-16:0-ACP and was much less active towards [1-$^{14}$C]-12:0-ACP and [1-$^{14}$C]-18:0-ACP substrates.

The methyl ester product of the [1-$^{14}$C]-14:0-ACP substrate had the same mobility on argentation TLC as that of a methyl ester standard for 14:1$\Delta^9$, suggesting that the type B gene product functioned as a $\Delta^9$ 14:0-ACP desaturase. The mobility of the [1-$^{14}$C]-16:0-ACP desaturation product on argentation TLC was also consistent with that of a $\Delta^9$ isomer. To confirm the position of the double bond placement, assays were repeated with a 15:0-ACP substrate. Because E. coli does not synthesize odd chain fatty acids, ambiguities caused by the presence of bacterial acyl-ACPs were eliminated. GC/MS analysis of the dimethyl disulfide adducts of 15:1 methyl esters from this assay showed that the double bond is placed at the $\Delta^9$ position of the 15:0-ACP substrate (FIG. 3.12). Collectively, results from the three assays with the recombinant protein, indicate that the type B gene product functions as a $\Delta^9$ 14:0-ACP desaturase.

Conclusion and Discussion

We have identified a novel acyl-ACP desaturase whose expression in inbred, pest-resistant geranium genotypes was closely correlated with pest resistance and the presence of the novel 16:1$\Delta^{11}$ and 18:1$\Delta^{13}$ fatty acids. To determine if the type B gene functions as a desaturase which could produce the novel 16:1$\Delta^{11}$ and 18:1$\Delta^{13}$ fatty acids, we expressed this gene in E. coli. Three distinct assays: (1) in vivo E. coli assays; (2) in vitro chain length specificity assay; and (3) the double bond position analysis of the in vitro product, lead us to conclude that the type B desaturase functions to place a double bond at the $\Delta^9$ position of a 14:0-ACP substrate. This represents the only report of a 14:0-ACP desaturase to date.

In E. coli control lines, the only unsaturated products detected are methyl esters of palmitoleic acid (16:1$\Delta^9$) and cis-vaccenic acid (18:1$\Delta^{11}$). Both of these unsaturated products result from the elongation of 10:1$\Delta^3$-ACP Magnuson et al., 1993). The efficiency of this elongation process in E. coli is evident, because the intermediates (12:1$\Delta^5$ or 14:1$\Delta^7$) are not detected (FIG. 3.9 A). In E. coli expressing the type B gene, the major additional fatty acids detected are 16:1$\Delta^{11}$ and 18:1$\Delta^{13}$, likely elongation products of a 14:1$\Delta^9$ fatty acid. In resistant geranium trichomes, we have also identified 16:1$\Delta^{11}$ and 18:1$\Delta^{13}$ fatty acids, but have not identified a 14:1$\Delta^9$ fatty acid (Yerger et al., 1992). We propose that the pest-resistant genotype is characterized by the production of 14:1$\Delta^9$ which is efficiently elongated, as in E. coli, to the two unique fatty acids 16:1$\Delta^{11}$ and 18:1$\Delta^{13}$ FIG. 3.13). A similar plant fatty acid elongation mechanism has been identified in the production of 18:1$\Delta^6$ fatty acids found in Coriandrum sativum (Cahoon and Ohlrogge, 1994). Based on biochemical analysis (Walters et al., 1990b; Hesk et al., 1992), the 16:1$\Delta^{11}$ and 18:1$\Delta^{13}$ fatty acids are the precursors to the 22:1 $\omega^5$ and 24:1 $\omega^5$ anacardic acids, respectively.

Small pest resistance in geranium is closely correlated with the presence of a single dominant locus that directs the production of $\omega^5$ anacardic acids. Several possibilities exist for the gene(s) encoded by this locus. One possibility is that the locus encodes the $\Delta^9$ 14:0-ACP desaturase gene we have isolated. Geranium is one of the few plants that remains recalcitrant to transformation. Limited success has been obtained transforming geranium; therefore it is not possible to complement the susceptible genotype with the novel desaturase gene to test the hypothesis that our gene is the dominant factor which controls resistance. An alternative possibility is that the dominant factor encodes a positive regulator that directly controls expression of the $\Delta^9$ 14:0-ACP desaturase gene (FIG. 3.13). Because expression of the $\Delta^9$ 14:0-ACP desaturase showed quantitative differences between homozygous and heterozygous pest-resistant plants, any putative positive regulator must interact quantitatively with our gene. Regardless of the scenario for the protein encoded by this dominant factor, the expression of the $\Delta^9$ 14:0-ACP desaturase gene is required for the production of the $\omega^5$ anacardic acids, and therefore is necessary for pest resistance.

Unsaturated anacardic acids provide a novel defense against pests. The identification of a trichome specific $\Delta^9$ 14:0-ACP desaturase defines the biosynthetic pathway of the specific $\omega^5$ anacardic acids which are necessary for pest resistance. Although plants produce a wide range of secondary metabolites, their effects on pests are largely unknown. Plant secondary metabolites and the genes encoding their biosynthetic enzymes represent a vast resource for future genetic engineering of plant pest resistance. The isolation and characterization of the novel $\Delta^9$ 14:0-ACP desaturase represents a step towards this goal.

In the larger context, the identification of the first novel 14:0-ACP desaturase and the gene therefor represents an important innovation in the development of unsaturated fatty acids and their expression and/or incorporation in natural and synthetic organisms and reactions.

Although the invention has been described with respect to particulars and specifics above, the invention is intended to be limited only insofar as is set forth in the accompanying claims.

TABLE 1

Composition of selected anacardic acids[z] in a backcross generation. These data are from analysis performed by David Hesk.

| Genotype | Classification | 22:0[z] | 22:1ω[5] | 24:0 | 24:1ω[5] | 24:1ω[9] |
|---|---|---|---|---|---|---|
| 88-47-01 | resistant | 5.7 | 44.8 | 5.9 | 27.1 | 0.0 |
| 88-47-09 | resistant | 6.7 | 43.2 | 4.9 | 24.1 | 0.0 |
| 88-47-10 | resistant | 5.6 | 41.8 | 6.9 | 25.8 | 0.0 |
| 88-47-21 | resistant | 5.7 | 27.6 | 12.4 | 27.5 | 0.0 |
| 88-47-22 | resistant | 6.7 | 42.5 | 6.2 | 23.4 | 0.0 |
| 88-47-24 | resistant | 5.5 | 42.5 | 6.6 | 26.1 | 0.0 |

TABLE 1-continued

Composition of selected anacardic acids[z] in a backcross generation. These data are from analysis performed by David Hesk.

| Genotype | Classification | 22:0[z] | 22:1ω[5] | 24:0 | 24:1ω[5] | 24:1ω[9] |
|---|---|---|---|---|---|---|
| 88-47-25 | resistant | 6.6 | 28.6 | 12.5 | 30.7 | 0.0 |
| 88-47-26 | resistant | 6.3 | 40.4 | 6.4 | 27.2 | 0.0 |
| 88-47-27 | resistant | 6.9 | 41.4 | 7.3 | 24.6 | 0.0 |
| 88-47-28 | resistant | 7.5 | 38.9 | 8.2 | 26.0 | 0.0 |
| 88-47-32 | resistant | 5.7 | 41.3 | 7.4 | 27.0 | 0.0 |
| 88-47-34 | resistant | 7.1 | 44.6 | 5.4 | 23.0 | 0.0 |
| 88-47-35 | resistant | 6.9 | 44.3 | 6.5 | 23.7 | 0.0 |
| 88-47-39 | resistant | 6.3 | 39.9 | 9.1 | 26.8 | 0.0 |
| 88-47-41 | resistant | 6.1 | 42.8 | 6.3 | 24.9 | 0.0 |
| 88-47-43 | resistant | 5.3 | 42.6 | 5.9 | 24.3 | 0.0 |
| 88-47-02 | susceptible | 25.3 | 0.4 | 22.6 | 0.0 | 8.3 |
| 88-47-03 | susceptible | 31.7 | 1.5 | 16.4 | 0.0 | 4.0 |
| 88-47-05 | susceptible | 24.2 | 0.2 | 23.7 | 0.0 | 8.1 |
| 88-47-06 | susceptible | 22.9 | 1.0 | 22.8 | 0.0 | 6.8 |
| 88-47-07 | susceptible | 30.4 | 0.6 | 18.5 | 0.0 | 3.9 |
| 88-47-08 | susceptible | 26.4 | 0.4 | 17.9 | 0.0 | 4.1 |
| 88-47-11 | susceptible | 23.0 | 0.3 | 20.8 | 0.0 | 10.9 |
| 88-47-42 | susceptible | 19.7 | 0.2 | 23.1 | 0.0 | 8.9 |
| 88-47-13 | susceptible | 18.4 | 0.4 | 19.6 | 0.0 | 10.5 |
| 88-47-14 | susceptible | 23.1 | 0.3 | 19.1 | 0.0 | 7.2 |
| 88-47-15 | susceptible | 26.3 | 0.3 | 22.6 | 0.0 | 6.3 |
| 88-47-16 | susceptible | 22.8 | 0.2 | 22.8 | 0.0 | 9.8 |
| 88-47-18 | susceptible | 23.2 | 0.6 | 16.1 | 0.0 | 9.5 |
| 88-47-19 | susceptible | 22.6 | 0.4 | 18.9 | 0.0 | 9.0 |
| 88-47-20 | susceptible | 29.0 | 0.3 | 19.6 | 0.0 | 5.5 |
| 88-47-23 | susceptible | 21.8 | 0.2 | 21.5 | 0.0 | 10.6 |
| 88-47-29 | susceptible | 25.8 | 0.5 | 17.6 | 0.0 | 6.9 |
| 88-47-33 | susceptible | 19.7 | 0.2 | 21.0 | 0.0 | 10.6 |
| 88-47-36 | susceptible | 22.1 | 0.6 | 24.8 | 0.0 | 5.9 |
| 88-47-37 | susceptible | 18.9 | 0.4 | 23.5 | 0.0 | 13.4 |
| 88-47-38 | susceptible | 26.9 | 0.4 | 19.4 | 0.0 | 6.6 |
| 88-47-40 | susceptible | 25.3 | 0.3 | 23.7 | 0.0 | 9.2 |
| 88-47-42 | susceptible | 28.5 | 0.6 | 17.4 | 0.0 | 4.1 |

[z]Values are represented as the % found within the entire profile.

TABLE 2

Phosphorimager Quantification of the Type B Desaturase Expression

| Tissue | rRNA[z] | Correction Term[y] | Type B Desaturase[x] | Corrected Value[w] | Fold Reduction |
|---|---|---|---|---|---|
| 1.) Resistant trichomes (homozygous) | 53.2 | 2.0 | 118.0 | 59.0 | 1.0 |
| 2.) Resistant trichomes (backcross - heterozygous) | 51.7 | 1.9 | 69.4 | 36.5 | 1.6 |
| 3.) Resistant pedicels (homozygous) | 74.0 | 2.7 | 5.2 | 1.9 | 31.0 |
| 4.) Resistant leaves (homozygous) | 67.9 | 2.5 | 2.2 | 0.9 | 65.6 |
| 5.) Susceptible trichomes (hdinozygous) | 50.6 | 1.9 | 3.7 | 1.9 | 31.0 |
| 6.) Susceptible trichomes (backcross - homozygous) | 27.2 | 1.0 | 2.8 | 2.8 | 21.1 |
| 7.) Susceptible pedicels (backcross - homozygous) | 33.8 | 1.2 | 1.7 | 1.4 | 42.1 |
| 8.) Susceptible leaves (homozygous) | 45.3 | 1.7 | 1.6 | 0.9 | 65.6 |

[z]Phosphorimager values for ribosomal probe
[y]The correction term was derived by dividing each value by the lowest value obtained (27.2 for suseptible trichomes - backcross).
[x]Phosphorimager values for the type B desaturase probe.
[w]The values obtained for the type B desaturase were divided by the corresponding correction term.
[v]Fold reduction was determined by dividing each corrected value into the corrected highest corrected value.

REFERENCES

Cahoon et al., "Expression of a coriander desaturase results in petroselinic acid production in transgenic tobacco," *Proc. Natl. Acad. Sci. USA*, 89:11184–11188 (1992).

Cahoon et al., "Metabolic evidence for the involvement of a Δ4-palmitoyl-acyl carrier protein desaturase in petroselinic acid synthesis in coriander endosperm and transgenic tobacco cells," *Plant Physiol*, 104:827–837 (1994).

Cahoon et al., "cDNAs for isoforms of the Δ$^9$-stearoyl-acyl carrier protein desaturase from Thunbergia alata endosperm," *Plant Physiol.*, 106:807–808 (1994).

Cahoon et al., "D6 hexadecenoic acid is synthesized by the activity of a soluble Δ6 palmitoyl-acyl carrier protein desaturase in *Thunbergia alata* endosperm," *J. Biol. Chem.*, 269:27519–27526 (1994).

Cahoon et al., "Modification of the Fatty Acid Composition of *Escherichia coli* by Co-Expression of a Plant Acyl—Acyl Carrier Protein Desaturase and Ferredoxin," *J. Bacteriol.*, 178:936–939 (1996).

Clark, Ph.D. Thesis, The Pennsylvania State University, University Park, Pa. (1995).

Craig et al., "Genetic control of a biochemical mechanism for mite resistance in geranium," In: *"Natural Resistance of Plants to Pests. Roles of Allelochemicals,"* Green, M. B. and P. A. Hedin. eds. American Chemical Society, Washington, D.C. (1986).

Gavel et al., "A conserved cleavage-site motif in chloroplast transit peptides," FEBS 261:455–458 (1990).

Gerhold et al., "Analysis of trichome exudate from mite resistant geraniums," *J. Chem. Ecol.* 10:713–722 (1984).

Grazzini et al., "Inhibition of lipoxygenase and prostaglandin endoperoxide synthase by anacardic acids." *Biochem. Biophys. Res. Comm.*, 176:775–780 (1991).

Grazzini, "A Biochemical, Evolutionary and Genetic Model of Glandular Trichome Mediated Small Pest Resistance in *Pelargonium xhortorum*," Ph.D. Thesis, The Pennsylvania State University (1993).

Grazzini et al., "Distribution of anacardic acids associated with small pest resistance among cultivars of *Pelargonium xhortorum,*" *J. Amer. Soc. Hort. Sci.*, 120:343–346 (1995).

Hesk et al., "Arthropod-resistant and -susceptible geraniums." In: *Naturally Occurring Pest Bioregulators*. Hedin. P. A. ed. American Chemical Society, Washington, D.C. (1991).

Hesk et al., "Comparison of the biosynthetic capability between resistant and susceptible geraniums," *J. Chem. Ecol.* 18:1349–1364 (1992).

Lutcke et al., Selection of AUG initiation codons differs in plants and animals, EMBO 6:43–48 (1987).

Magnuson et al., "Regulation of fatty acid biosynthesis in *Escherichia coli.,*" *Microbiol. Rev.*, 57:522 –542. (1993).

Rock et al., *J. Biol. Chem.*, 254:7123–7128 (1979).

Sambrook et al., *Molecular Cloning Manual. A Laboratory Manual*, Cold Spring Harbor Laboratory Press, Cold Spring Harbor (1989).

Walters et al., "Geranium defensive agents. IV. Chemical and morphological bases of resistance," *J. Chem. Ecol.*, 15:357–372 (1989).

Walters et al., "Glandular trichome exudate is the critical factor in geranium resistance to foxglove aphid," *Entomol. exp. appl.*, 53:105–109 (1989).

Walters et al., "Heritable trichome exudate differences of resistant and susceptible geraniums," In: *Pesticides and Alternatives: Innovative Chemical and Biological Approaches to Pest Control*. Casida J. E. ed. Elsevier Science Publishers BV, Amsterdam, The Netherlands (1990).

Walters et al., "Fatty acid incorporation in the biosynthesis of anacardic acids of geraniums," *Phytochemistry*, 29:1815–1822. (1990).

Walters et al., "Effects of mite resistance mechanism of geraniums on mortality and behavior of foxglove aphid (*Acyrthosiphon solani* Kaltenbach)," *J. Chem. Ecol.*, 16:877–886 (1990).

We claim:

1. An isolated and purified DNA nucleotide sequence comprising:
   (a) the nucleotide sequence set forth in SEQ. ID. NO. 1 or
   (b) a nucleotide sequence encoding the polypeptide set forth in SEQ. ID. NO. 2,
   wherein said nucleotide sequence encodes a 14:0-ACP desaturase.

2. A method of making mRNA encoding a 14:0-ACP desaturase comprising growing a cell or plant having integrated in its genome a DNA sequence having the nucleotide sequence set forth in SEQ. ID. NO. 1 or having a nucleotide sequence encoding the polypeptide set forth in SEQ. ID. NO. 2 under conditions which permit transcription of the 14:0-ACP desaturase encoding sequence.

3. The method according to claim 2 wherein said cell or plant is a garden geranium and wherein expression of the gene leads in turn to pest resistance of said geranium.

4. The method according to claim 2 wherein said cell or plant is selected from the group of plants consisting of soybeans, rapeseed, maize, sunflower, safflower, cotton, cuphea, peanut, coconut and oil-palm and wherein as a result of gene expression the oil therein contains a higher percentage of unsaturated fatty acids.

5. A nucleic acid vector, comprising one of:
   a) the nucleotide sequence set forth in SEQ ID NO. 1; or
   b) a nucleotide sequence encoding the polypeptide set forth in SEQ ID NO: 2.

6. A cell transformed with the vector as claimed in claim 5.

7. A method for making 14:0-ACP desaturase comprising the step of growing a cell as claimed in claim 6 under conditions which permit expression of the 14:0-ACP desaturase encoding sequence of the vector.

* * * * *